(12) United States Patent
Nakase et al.

US011324831B2

(10) Patent No.: US 11,324,831 B2
(45) Date of Patent: May 10, 2022

(54) METHOD FOR INTRODUCING EXOGENOUS SUBSTANCE INTO CELL, AND MATERIAL USED IN SAID METHOD

(71) Applicants: TOAGOSEI CO., LTD, Tokyo (JP); OSAKA PREFECTURE UNIVERSITY PUBLIC CORPORATION, Osaka (JP)

(72) Inventors: Ikuhiko Nakase, Tokyo (JP); Tetsuhiko Yoshida, Tokyo (JP); Nahoko Baileykobayashi, Tokyo (JP)

( * ) Notice: Subject to any disclaimer, the term of this patent is extended or adjusted under 35 U.S.C. 154(b) by 617 days.

(21) Appl. No.: 15/585,228

(22) Filed: May 3, 2017

(65) Prior Publication Data
US 2017/0246304 A1 Aug. 31, 2017

Related U.S. Application Data

(63) Continuation of application No. PCT/JP2015/081709, filed on Nov. 11, 2015.

(30) Foreign Application Priority Data

Nov. 13, 2014 (JP) .............................. JP2014-230472

(51) Int. Cl.
*A61K 47/46* (2006.01)
*A61K 38/18* (2006.01)
*A61P 35/00* (2006.01)
*A61P 43/00* (2006.01)
*A61K 9/50* (2006.01)

(52) U.S. Cl.
CPC ............ *A61K 47/46* (2013.01); *A61K 9/5063* (2013.01); *A61K 38/1808* (2013.01)

(58) Field of Classification Search
CPC ..... A61K 47/46; A61K 38/1808; A61P 35/00; A61P 43/00
See application file for complete search history.

(56) References Cited

U.S. PATENT DOCUMENTS

| 2003/0082234 | A1 | 5/2003 | Seo et al. | |
| 2004/0023322 | A1* | 2/2004 | Goodheart | C07K 14/51 435/69.1 |
| 2008/0317844 | A1 | 12/2008 | Dudley et al. | |
| 2016/0346334 | A1* | 12/2016 | Trujillo | A61K 35/12 |

FOREIGN PATENT DOCUMENTS

| JP | 2003517886 | 6/2003 |
| JP | 2013063926 | 4/2013 |
| JP | 2013063926 A | 4/2013 |
| JP | 2013121986 | 6/2013 |
| WO | WO2011/109677 | 9/2011 |

OTHER PUBLICATIONS

Schafer, A., et al. Disconnecting the Yin and Yang relation of epidermal growth factor receptor (EGFR)-mediated delivery: A fully synthetic, EGFR-targeted gene transfer system avoiding receptor activation. Human Gene Therapy, 2011, vol. 22, p. 1463-1473.*
Lai, R.C. et al. Exosomes for drug delivery—a novel application for the mesenchymal stem cell. Biotechnology Advances, 2013, 31: 543-551.*
Marquez, L., et al. Enhanced bone healing of rat rooth sockets after administration of epidermal growth factor (EGF) carried by liposome. Injury, 2013, 44:558-564.*
Van Horssen, R., et al. TNF-alpha in cancer treatment: molecular insights, antitumor effects, and clinical utility. The Oncologist, 2006, 11:397-408.*
Kruth et al., The Journal of Biological Chemistry, vol. 280, 2005, pp. 2352-2360, Jan. 21, 2005.
Nakase et al., English translation of "Abstracts of 37th Annual Meeting of Membrane Society of Japan, pp. 74", Apr. 21, 2015.
Ohno, S. et al., Systematically injected exosomes targeted to EGFR deliver antitumor microRNA to breast cancer cells. Mol Ther., Jan. 2013, 21(1), p. 185-91, Epub Oct. 2, 2012, particularly, p. 186-6.
Tanaka, G. et al., CXCR4 stimulates macropinocytosis: implications for cellular uptake of arginine-rich cell-penetrating peptides and HIV, Chem Biol., Nov. 21, 2012, 19(11), p. 1437-46, particularly, p. 1437-8.
Nakase, I. et al., Active macropinocytosis induction by stimulation of epidermal growth factor receptor and oncogenic Ras expression potentiates cellular uptake efficacy of exosomes, Sci Rep., Jun. 3, 2015,5:10300.
Ikuhiki Nakase et al., "Macropinocytosis Yudo ni yoru Exosome no Saibonai Iko Sokushin", Abstracts of 37th Annual Meeting of Membrane Society of Japan, Apr. 21, 2015 (Apr. 21, 2015), p. 74.
Chemistry & Biology, vol. 19, 2012, pp. 1437-1446.
The Journal of Biological Chemistry, vol. 289, 2014, pp. 22258-22267.
Journal of Cell Science, vol. 94, 1989, pp. 135-142.
Jul. 11, 2019 Office Action Japanese Application No. 2016-559084.
Jan. 29, 2020 Office Action Japanese Application No. 2016-559084.

* cited by examiner

*Primary Examiner* — Ruixiang Li
(74) *Attorney, Agent, or Firm* — Lambert Shortell & Connaughton; David J. Connaughton, Jr.; Justin P. Tinger

(57) ABSTRACT

Provided is a novel material used to introduce an exogenous substance into cells. Also provided is a method for introducing an exogenous substance into target cells using this material. The present invention provides an exosome that is used to introduce an exogenous substance into target cells, wherein the exosome contains one type or two or more types of an exogenous substance and a substance that induces macropinocytosis in the target cells. The present invention also provides a composition containing the exosome and a method for introducing an exogenous substance into cells using this exosome.

7 Claims, 15 Drawing Sheets

METHOD FOR INTRODUCING EXOGENOUS SUBSTANCE INTO CELL, AND MATERIAL USED IN SAID METHOD

TECHNICAL FIELD

The present invention relates to a method for introducing an exogenous substance into a cell and a material used in that method. More particularly, the present invention relates to a method for introducing an exogenous substance into a cell using uptake of an exosome by macropinocytosis, and a material used in that method.

Furthermore, the present application claims priority on the basis of Japanese Patent Application No. 2014-230472 filed on Nov. 13, 2014, the contents of which are incorporated herein in their entirety by reference.

BACKGROUND ART

The development of technology for spatially, chronologically and quantitatively controlling the distribution of a drug in the body is an extremely important issue in the field of pharmaceuticals. Preferably controlling the distribution of a drug in the body makes it possible to, for example, enhance drug efficacy, mitigate adverse side effects, decrease the required number of administrations and reduce costs. Technology for spatially, chronologically and quantitatively controlling the distribution of a drug in the body in this manner is generally referred to as a drug delivery system (DDS), and extensive research is currently being conducted in this field.

Attention has recently been focused on technology relating to DDS at the cellular level, and typically technology for efficiently introducing an exogenous substance into a target cell. The application of this technology makes it possible to efficiently supply (or allow to act) a target drug on the causative cell of a disease, for example. In particular, if it were possible to only allow a drug having potent adverse side effects on normal cells (such as an anticancer drug) to efficiently act on target cells (such as cancer cells), a high level of efficacy would be able to be realized while reducing adverse side effects.

In addition, this technology relating to DDS at the cellular level is also attracting considerable attention in the field of regenerative medicine. For example, the application of this technology enables a reprogramming factor, differentiation-inducing factor, etc., to be efficiently introduced into a target cell. In addition, when grafting a graft material for regenerative medicine (such as stem cells used in regenerative medicine or cells and tissue induced to differentiate from these stem cells) into the body, this technology can be applied to efficiently supply factors to the graft material that are required until the graft material becomes established in the body.

Patent Literature 1 to 3 describe technologies relating to DDS at the cellular level in the form of techniques for introducing a desired substance (and typically, a drug) into a cell using various carrier substances.

CITATION LIST

Patent Literature

Patent Literature 1: Japanese Patent Application Laid-open No. 2013-121986
Patent Literature 2: Japanese Patent Application Laid-open No. 2013-063926
Patent Literature 3: Japanese Translation of PCT Application No. 2003-517886

Non Patent Literature

Non Patent Literature 1: Chemistry & Biology, Vol. 19, 2012, pp. 1437-1446
Non Patent Literature 2: The Journal of Biological Chemistry, Vol. 289, 2014, pp. 22258-22267
Non Patent Literature 3: Journal of Cell Science, Vol. 94, 1989, pp. 135-142

SUMMARY OF INVENTION

However, in the conventional DDS described in Patent Literature 1 to 3, for example, compounds used in vitro are typically used as carrier substances for introducing an exogenous substance into a cell. When such an in vitro compound is used, there are cases in which adequate effects are unable to be demonstrated due to cytotoxicity attributable to the carrier or an immune response to the carrier.

Consequently, attempts have been made to establish a technology for introducing an exogenous substance into a cell using a bio-derived substance.

With the foregoing in view, the present invention was conceived for the purpose of providing a novel material used to introduce an exogenous substance into a cell. More specifically, an object of the present invention is to establish a technology for introducing an exogenous substance into the body using a bio-derived substance. In addition, another object of the present invention is to provide a method for introducing an exogenous substance into a target cell using that material.

The inventors of the present invention focused on exosomes, which are widely distributed throughout the body, as a means for achieving these objects. Exosomes refer to vesicles present in the body (and typically, in body fluids) that are formed from a lipid bilayer membrane. As a result of conducting extensive research on the mechanism by which exosomes are taken up into cells, the inventors of the present invention found that exogenous substances contained in exosomes can be preferably introduced into a target cell by inducing macropinocytosis in a target cell. Moreover, the inventors of the present invention newly found that the uptake of an exosome into a target cell is promoted by supplying the target cell with an exosome containing a substance that induces macropinocytosis. The inventors of the present invention completed the present invention on the basis of these findings.

Non Patent Literature 1 describes a phenomenon in which macropinocytosis is activated by supplying a cell with a substance that stimulates a specific receptor, while Non Patent Literature 2 describes a phenomenon in which exosomes are taken up into cells by macropinocytosis. However, there are no disclosures or suggestions that an exogenous substance contained in an exosome can be preferably introduced into a target cell by inducing macropinocytosis or that the uptake of an exosome into a cell is promoted by supplying the cell with an exosome containing a substance that induces macropinocytosis.

In order to realize these objects, the present invention provides an exosome having the ability to introduce an exogenous substance into a target cell (and this exosome is also referred to as an "exosome for introducing an exogenous substance") when the exosome is supplied to the target cell (and typically, when added to a medium used to culture the target cell).

Namely, the exosome disclosed herein (exosome for introducing an exogenous substance) is an exosome used to introduce an exogenous substance into a target cell from outside the target cell, containing:

one type or two or more types of an exogenous substance; and a substance that induces macropinocytosis in the target cell.

The exosome for introducing an exogenous substance disclosed herein is characterized by containing a substance that induces macropinocytosis in the exosome along with an exogenous substance. As a result thereof, macropinocytosis can be induced (activated) in a target cell and uptake of the exosome by the target cell can be promoted. Thus, an exogenous substance contained in an exosome for introducing an exogenous substance can be efficiently introduced into a target cell.

Here, an exosome refers to a bio-derived substance. Consequently, cytotoxicity attributable to the exosome and an immune response to the exosome can be reduced in comparison with a substance derived from an in vitro compound. Consequently, the exosome is preferable as a carrier for introducing an exogenous substance.

In addition, since the exosome for introducing an exogenous substance disclosed herein contains a target exogenous substance and a substance that induces macropinocytosis therein, it is not necessary to provide or manipulate the substance inducing macropinocytosis and the exosome containing the exogenous substance, or carry out procedures for mixing these substances. Consequently, a target exogenous substance can be introduced into a target cell by a simple procedure including supplying an exosome for introducing an exogenous substance into the target cell.

In addition, exosomes are vesicles that are able to stably maintain the structure thereof in cell culture broth. In addition, they are resistant to decomposition and are stable in the body (such as in blood). Consequently, by containing a substance that induces macropinocytosis and an exogenous substance in an exosome, the decomposition (including metabolism and deactivation) thereof can be reduced. For example, metabolism of a drug in the liver, excretion as waste and elimination by immune cells can be preferably reduced (avoided). Thus, the exosome for introducing an exogenous substance disclosed herein is able to stably supply a substance inducing macropinocytosis and an exogenous substance into a cell (and particularly a cell in the body).

Consequently, the exosome for introducing an exogenous substance disclosed herein is preferable as a component of a composition used in an application for introducing an exogenous substance into a target cell. In addition, it can also be used in a method for introducing an exogenous substance into a target cell.

In a preferable mode of the exosome (exosome for introducing an exogenous substance) disclosed herein, the substance that induces macropinocytosis in the target cell is a substance that stimulates (activates) epidermal growth factor receptor (EGFR) or a substance that stimulates (activates) CXC chemokine receptor 4 (also referred to as CXCR4, CD184 or fusin).

Epidermal growth factor receptor and CXC chemokine receptor 4 are typical examples of receptors capable of inducing macropinocytosis following stimulation thereof. Consequently, substances that stimulate (activate) epidermal growth factor receptor and substances that stimulate (activate) CXC chemokine receptor 4 are preferable as substances for inducing macropinocytosis.

In particular, an exosome containing EGF or an analog thereof or containing stromal cell-derived factor (SDF) or an analog thereof for the substance that induces macropinocytosis in a target cell is a preferable mode of the exosome (exosome for introducing an exogenous substance) disclosed herein. EGF or an analog thereof is a substance that preferably stimulates epidermal growth factor receptor, while SDF or an analog thereof is a substance that preferably stimulates CXC chemokine receptor 4.

In general, chemokines have four cysteine residues (C) preserved within a molecule thereof, and are classified into four subfamilies (C, CC, CXC and CX3C) according to differences in the relationship between the two cysteine residues on the N-terminal side and other amino acid residues. Among these, CXC chemokines refer to chemokines belonging to the subfamily having an amino acid sequence ("C-X-C" sequence) in which a single arbitrary amino acid residue (X) is present between the two cysteine residues (C) on the N-terminal side.

In a preferable mode of the exosome (exosome for introducing an exogenous substance) disclosed herein, the exogenous substance has pharmacological activity. As a result of employing this configuration, a substance having pharmacological activity can be efficiently supplied to a target cell. As a result, the pharmacological effect of the substance having pharmacological activity can be demonstrated at a high level.

In a preferable mode of the exosome (exosome for introducing an exogenous substance) disclosed herein, the target cell is a human tumor cell and the exogenous substance is a compound having antitumor activity. Many compounds having antitumor activity typically have potent adverse side effects on normal cells. According to this mode, since a compound having antitumor activity can be efficiently supplied to a human tumor cell, antitumor activity can be demonstrated at a high level on the tumor cell while reducing adverse side effects on normal cells attributable to the compound having antitumor activity.

In addition, in another aspect thereof, the present invention provides a composition (pharmaceutical composition) used to introduce an exogenous substance into a target cell from outside the target cell (this composition may also be referred to as a "composition for introducing an exogenous substance"), comprising:

one type or two or more types of a pharmaceutically acceptable carrier;

a substance that induces macropinocytosis in the target cell; and an exosome containing one type or two or more types of an exogenous substance.

Since the composition having this configuration (composition for introducing an exogenous substance) contains a substance that induces macropinocytosis, uptake of an exosome into a target cell can be preferably promoted. As a result, an exogenous substance contained in the exosome can be efficiently introduced into a target cell.

In addition, in another aspect thereof, the present invention provides a composition (pharmaceutical composition) used to introduce an exogenous substance into a target cell from outside the target cell (composition for introducing an exogenous substance), comprising:

one type or two or more types of a pharmaceutically acceptable carrier; and an endosome containing a substance that induces macropinocytosis in the target cell and one type or two or more types of an exogenous substance.

Since the composition of this configuration (composition for introducing an exogenous substance) contains a substance that induces macropinocytosis in an exosome, uptake of the exosome into the target cell can be preferably promoted. As a result, the exogenous substance contained in the exosome can be efficiently introduced into the target cell. Moreover, since a substance that induces macropinocytosis in the target cell is contained within the exosome, the substance that induces macropinocytosis can be stably supplied to the target cell.

In addition, in another aspect thereof, the present invention provides a method for introducing an exogenous substance into a target cell in vitro, comprising:

preparing a cell culture containing the target cell; and supplying an exosome containing a substance that induces macropinocytosis in the target cell and one type or two or more types of an exogenous substance to the cell culture.

According to this method for introducing an exogenous substance, an exogenous substance can be efficiently introduced into a target cell by an easy method including supplying an exosome to a culture containing the target cell (and typically, the medium used to culture the target cell). In addition, by using an exosome that is a bio-derived substance as a carrier for introducing an exogenous substance into a cell, cytotoxicity due to the carrier can be reduced.

DESCRIPTION OF EMBODIMENTS

Figure 1:
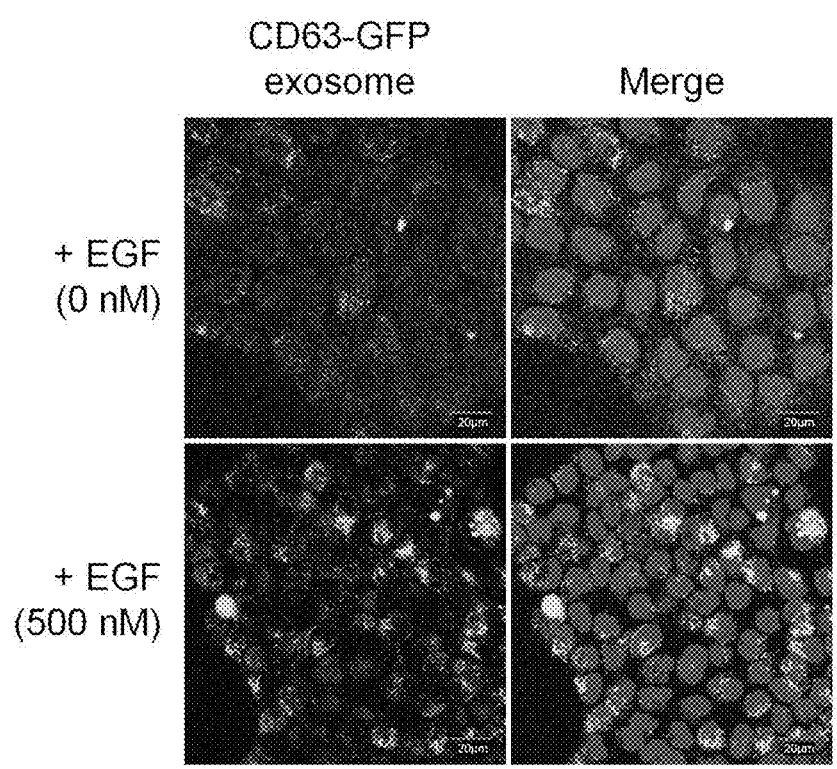
FIG. 1 depicts micrographs (images) captured using a confocal laser scanning microscope for investigating the uptake of exosomes by target cells (A431 cells) when exosomes (Sample 1) were supplied to the target cells in a test example and then cultured in the presence and absence of EGF. The micrographs (images) shown on the left (CD63-GFP exosome column) are fluorescent light micrographs (FL images) for investigating the localization of exosomes by fluorescent observation. In addition, the micrographs (images) shown in the right column (Merge column) are merged images obtained by superimposing (merging) the FL images shown in the left column with nuclear staining images obtained using Hoechst 33342. Furthermore, the scales shown in the micrographs are all 20 μm.

The following provides an explanation of preferred embodiments of the present invention. Matters required for working the present invention (such as general matters relating to methods for synthesizing and acquiring a desired exogenous substance, methods for culturing cells or the preparation of pharmaceutical compositions) other than those specifically mentioned in the present description (such as the configuration of the exosome for introducing an exogenous substance or the composition for introducing an exogenous substance disclosed herein) can be understood to be design matters for a person with ordinary skill in the art based on conventional technology in fields such as cell engineering, physiology, medicine, pharmacology, organic chemistry, biochemistry, genetic engineering, protein engineering, molecular biology or genetics. The present invention can be carried out based on the contents disclosed in the present description and common general technical knowledge in the art.

In addition, the entire contents of all literature cited in the present description are incorporated in the present description by reference.

In the present description, "exosome" refers to a vesicle formed from a lipid bilayer membrane that is secreted outside the cells from various eukaryotic cells. It is typically a vesicle having a diameter of about 50 nm to 100 nm. Exosomes are clearly distinguished from liposomes (artificially fabricated vesicles modeled after the cell membrane) in that exosomes are vesicles secreted by cells (or in other words, are bio-derived substances).

There are no particular limitations on the cells that secrete exosomes, and for example, various cultured cells (such as cell lines or primary cultured lines) and various cells present in the body (such as epithelial cells, fibroblasts, muscle cells, immune cells or hematopoietic cells) are able to secrete exosomes. Not only normal cells but also tumor cells and pathogen-infected cells are able to secrete exosomes. These exosomes are present in medium used to culture cells and in various body fluids of the body. Examples of these body fluids include blood (and typically, serum or plasma), saliva, urine, ascites, bone marrow and amniotic fluid. Exosomes are stable in these body fluids and culture broths (without their contents being decomposed in the body fluid).

In the present description, "macropinocytosis" refers to a type of endocytosis by which an extracellular substance (including extracellular fluid) is taken up into a cell in a form in which the cell membrane is made to protrude outward due to polymerization of actin (actin filaments) located around the cell membrane. Typically, a phenomenon in which the cell membrane appears wavy (membrane ruffling) is observed.

Here, macropinocytosis is clearly distinguished from endocytosis, in which an extracellular substance is taken up into a cell in a form in which the cell membrane invaginates into the cell, in the manner indicated below. This cell membrane invagination type of endocytosis typically proceeds dependent on the amount of clathrin protein on the surface of the cell membrane. Consequently, this type of endocytosis is also referred to as clathrin-dependent endocytosis. On the other hand, macropinocytosis is not dependent on clathrin protein. In addition, in contrast to endosomes formed by clathrin-dependent endocytosis having a diameter of about 100 nm, endosomes formed by macropinocytosis (also referred to as macropinosomes) have a larger diameter of about 200 nm to 5000 nm (0.2 μm to 5 μm).

In the present description, an "exogenous substance" refers to an exogenous substance as viewed from the target cell to which the present invention is applied. Namely, in the case the target cell is a cultured cell maintained in an in vitro culture system, there is no distinction made between whether or not a substance is exogenous in an organism from which the target cultured cell has been isolated. For example, substances introduced into cultured target cells from outside the cells can all be said to be exogenous substances. For example, even a substance isolated from the same cell line as the cultured cells can be said to be an exogenous substance relative to the target cells if that the substance is introduced into the cells from outside the cells. In addition, the question of whether or not a substance in a body (individual) in which a target cell is present is an exogenous substance is not an issue if the target cell is present within the body. For example, not only substances artificially synthesized outside a body in which a target cell is present and substances derived from an organism other than the body in which the target cell is present, but also substances isolated from a body in which the target cell is present (same individual) are typical examples of exogenous substances.

The exosome disclosed herein is an exosome discovered for the first time by the inventor of the present that can be used to introduce an exogenous substance into a target cell. As was previously described, the exosome (exosome for introducing an exogenous substance) disclosed herein contains one type or two or more types of an exogenous substance and a substance that induces macropinocytosis in the target cell (also referred to as a "macropinocytosis-inducing substance"). Namely, the exosome for introducing an exogenous substance disclosed herein typically contains a carrier in the form of an exosome granule, an exogenous substance contained in the exosome granule, and a macropinocytosis-inducing substance also contained in the exosome granule. The following provides an explanation of each of the substances that form this exosome for introducing an exogenous substance.

<Exosome>

An exosome secreted from various cells can be recovered and used as an exosome used for the exosome for introducing an exogenous substance disclosed herein (namely a carrier in the form of an exosome granule). For example, bio-derived exosomes are present in body fluids such as blood (and typically, serum), urine, saliva, lymph, gastrointestinal fluid, pulmonary lavage fluid, cerebrospinal fluid, inflammatory exudate, amniotic fluid or breast milk. Consequently, this body fluid can be collected and exosomes present therein can be recovered and used. Alternatively, since exosomes released (secreted) from cultured cells are present in the culture broth used to culture the cells, exosomes recovered from the cell culture broth can also be used without any particular limitations.

Furthermore, exosomes recovered from body fluid and exosomes recovered from cell culture broth can be used without distinction in the present invention from the viewpoint of introducing an exogenous substance into a target cell, and can be suitably selected and used. Exosomes recovered from cell culture broth are used preferably from the viewpoint of efficiently recovering (preparing) the required amount of exosomes.

In addition, the properties of an exosome may differ depending on the type of cell that excretes the exosomes, examples of which include the profile of the lipid bilayer membrane that forms the exosome (such as the composition of peptides (including proteins), lipids or saccharides contained in the lipid bilayer membrane), and the composition of substances inherently contained in the exosome (such as peptides (including proteins), RNA (such as mRNA or microRNA) or soluble components contained in cytoplasm). Consequently, in the case of using an exosome having specific properties, it is preferable to use an exosome that has been recovered from a cell broth in which specific cells are cultured. As a result, exosomes having similar properties can be acquired in a highly pure state.

Alternatively, a specific molecule may be imparted to the surface of the membrane forming an exosome using a genetic engineering technique and the like. For example, a target molecule can be imparted to the surface of the membrane forming an exosome by forcibly expressing a specific molecule (such as a peptide or protein) on the cell membrane surface of a cell that secretes the exosome (exosome-producing cell). The use of a molecule for the specific molecule that acts with a molecule forcibly expressed in a target cell (and typically, a molecule that binds to a receptor strongly expressed in a target cell) enables an exogenous substance to be introduced into the target cell. Namely, specificity for the target cell improves, thereby making this preferable.

A conventionally known method can be used for the method used to recover exosomes from body fluid or cell culture broth as previously described. For example, exosomes can be isolated by ultracentrifugal separation (Thery, C., Curr. Protoc. Cell Biol. (2006), Chapter 3, Unit 3.22). Alternatively, exosomes may be isolated using a commercially available reagent (kit) such as Total Exosome Isolation (from cell culture media) (Life Technologies Corporation (Invitrogen)). Exosomes can also be recovered from body fluid or cell culture broth by a method using antibody to a marker protein specific to exosomes (such as CD9, CD63 or CD81), or by a method that uses a suitable filter or column (such as a filter method or column method). Examples thereof include immunoprecipitation, FACS, ultrafiltration, gel filtration, filtering, HPLC or methods that separate exosomes adsorbed to a polymer or beads using precipitation or a column.

Examples of methods used to confirm recovery of exosomes according to the methods described above include a method including observing using a transmission electron microscope (and typically, negative staining), and a method including detecting an exosome marker protein (such as CD9, CD63 or CD81) by a technique such as western blotting, ELISA or FACS (typically immunological techniques). Alternatively, exosome-derived RNA may be measured.

In the present description, the amount of exosomes (g) recovered according to the methods described above is indicated as the total amount of protein of the recovered exosomes. Namely, the amount of recovered exosomes (g) can be calculated by measuring the total weight of protein present in a dispersion of recovered exosomes. More specifically, in the case 1 μg/mL of total protein is contained in a dispersion of recovered exosomes, this is treated as containing 1 μg/mL of exosomes in the exosome dispersion.

<Macropinocytosis-Inducing Substance>

There are no particular limitations on the macropinocytosis-inducing substance used for the exosome for introducing an exogenous substance disclosed herein provided it is a substance capable of inducing macropinocytosis in a target cell.

Examples thereof include substances that stimulate (activate) epidermal growth factor receptor (EGFR) and substances that stimulate (activate) CXC chemokine receptor 4 (CXCR4). Alternatively, other examples include substances that stimulate (activate) platelet-derived growth factor receptor (PDGFR) and substances that stimulate (activate) fibroblast growth factor receptor (FGFR) and/or Syndecan-4. EGFR, CXCR4 and PDGFR are all receptors capable of inducing macropinocytosis as a result of stimulation (activation) thereof. In addition, FGFR and Syndecan-4 are receptors capable of inducing macropinocytosis as a result of stimulation (activation) of these receptors (or complexes of these receptors).

Alternatively, substances known to be able to induce macropinocytosis without requiring stimulation of a specific receptor can also be used as macropinocytosis-inducing substances. Examples thereof include substances that activate intracellular protein kinase C (PKC) without requiring stimulation of a specific receptor. Non Patent Literature 3 describes that macropinocytosis can be induced by activating intracellular PKC of a target cell.

Here, a substance conventionally known to activate EGFR can be used without any particular limitations for the substance that activates EGFR. A substance known to be a ligand of EGFR can typically be used. Here, examples of ligands of EGFR include epidermal growth factor (EGF), transforming growth factor-α (TGF-α), heparin-binding epidermal growth factor-like factor (HB-EGF), amphiregulin (AREG or AR), betacellulin (BTC), epiregulin (EREG) and epigen (EPG).

EGFR ligands and analogs thereof are substances that can be preferably used as macropinocytosis-inducing substances. Alternatively, agonists of these EGFR ligands and analogs thereof can also be preferably used as macropinocytosis-inducing substances.

Among these, since EGF and analogs thereof as well as EGF agonists and analogs thereof have superior ability to induce macropinocytosis by stimulating EGFR, they can be preferably used as macropinocytosis-inducing substances. EGF and analogs thereof are particularly preferable for carrying out the present invention.

In addition, substances conventionally known to activate CXCR4 can be used without any particular limitations as substances that stimulate CXCR4. A substance known to be a ligand of CXCR4 can typically be used. Here, examples of substances that stimulate CXCR4 (and typically, ligands of CXCR4) include stromal cell-derived factor-1 (SDF-1).

Ligands of CXCR4 (and typically, SDF-1) and analogs thereof can be preferably used as macropinocytosis-inducing substances. Alternatively, agonists of CXCR4 ligands (and typically, SDF-1) and analogs thereof can also be preferably used as macropinocytosis-inducing substances. SDF-1 and analogs thereof are particularly preferable for carrying out the present invention.

In addition, a substance conventionally known to activate PDGFR can be used without any particular limitations for the substance that activates PDGFR. A substance known to be a ligand of PDGFR can typically be used. Here, examples of substances that stimulate PDGFR (and typically, ligands of PDGFR) include platelet-derived growth factor (PDGF).

PDGFR ligands (and typically, PDGF) and analogs thereof can be preferably used as macropinocytosis-inducing substances. Alternatively, agonists of these PDGFR ligands (and typically, PDGF) and analogs thereof can also be preferably used as macropinocytosis-inducing substances. PDGF and analogs thereof are particularly preferable for carrying out the invention.

In addition, substances conventionally known to activate either of at least FGFR and Syndecan-4 can be used without any particular limitations for the substance that stimulates FGFR and/or Syndecan-4. Substances known to be ligands of FGFR and Syndecan-4 can typically be used. Here, examples of substances that stimulate FGFR and Syndecan-4 (and typically, ligands of FGFR) include fibroblast growth factor (FGF).

Ligands of FGFR and Syndecan-4 (and typically, FGF) and analogs thereof can be preferably used as macropinocytosis-inducing substances. Alternatively, agonists of FGFR and Syndecan-4 ligands (and typically, FGF) and analogs thereof can also be preferably used as macropinocytosis-inducing substances. FGF and analogs thereof are particularly preferable for carrying out the present invention.

In addition, substances conventionally known to activate PKC within cells can be used without any particular limitations as substances that activate PKC within those cells without requiring stimulation of a specific receptor as described above. Examples of substances that activate PKC within cells include phorbol esters (and specifically, phorbol 12-myristate 13-acetate (PMA). Phorbol esters (and typically, PMA) are substances that are known to induce macropinocytosis as a result of activation of PKC within cells (Non Patent Literature 3).

The macropinocytosis-inducing substance can be suitably selected corresponding to the target cell. For example, if the target cell is a cell expressing EGFR (and typically, a cell highly expressing EGFR), then a substance that stimulates EGFR can preferably be used for the macropinocytosis-inducing substance. In addition, if the target cell is a cell that expresses CXCR4 (and typically, a cell highly expressing CXCR4), then a substance that stimulates CXCR4 can preferably be used for the macropinocytosis-inducing substance. Similar to these cases of EGFR and CXCR4, if the target cell is a cell that expresses PDGFR (and typically, a cell highly expressing PDGFR), then a substance that stimulates PDGFR can preferably be used for the macropinocytosis-inducing substance, and if the target cell is a cell that expresses FGFR and/or Syndecan-4 (and typically, a cell highly expressing FGFR and/or Syndecan-4), then a substance that stimulates FGFR and/or Syndecan-4 can preferably be used for the macropinocytosis-inducing substance.

The substance that induces macropinocytosis disclosed herein may be in the form of any salt provided the ability thereof to induce macropinocytosis in the target cell is not impaired. For example, acid addition salts can be used that are obtained by adding and reacting a commonly used inorganic acid or organic acid in accordance with ordinary methods. Alternatively, other salts (such as metal salts) may also be used provided they have the ability to induce macropinocytosis in the target cell. Thus, a "substance that induces macropinocytosis" as described in the present description and claims includes that in the form of these salts.

Furthermore, a substance acquired by purchasing a commercially available product can be used for the substance that induces macropinocytosis (and typically, a substance that stimulates EGFR, a substance that stimulates CXCR4, a substance that stimulates PDGFR, a substance that stimulates FGFR and Syndecan-4 or a substance that activates PKC). Alternatively, the substance may also be that produced according to a known method. For example, the substance can be a substance that has been artificially synthesized by chemical synthesis or biosynthesis (such as that produced based on genetic engineering). Furthermore, a detailed explanation of methods used to acquire the substance inducing macropinocytosis is omitted since it does not characterize the present invention.

<Exogenous Substance>

The exosome for introducing an exogenous substance disclosed herein contains one type or two or more types (such as 3 or more types) of a desired exogenous substance therein. There are no particular limitations on the exogenous substance provided it is a substance that is desired to be introduced into a target cell. A substance that has some forms of physiological activity (and typically, pharmacological activity) is preferable due to the high utility value thereof in the health care industry. A substance that demonstrates a therapeutic effect against a specific disease is preferable for the exogenous substance from the viewpoint of using the exosome for introducing an exogenous substance for the purpose of treating that disease. For example, the substance can be a substance used as a pharmaceutical or active ingredient of a pharmaceutical. There are no particular limitations on the pharmaceutical or active ingredient thereof provided it is a substance for which the use thereof is recognized to be that of a pharmaceutical, and examples thereof include chemically synthesized drugs (and typically, low molecular weight drugs), drugs applying biotechnology (so-called biologics) and herbal medicines (such as Chinese herbal medicines).

The physiological activity (and typically, pharmacological activity) possessed by the exogenous substance can be a property that acts on a specific physiological regulatory function of a target cell. Alternatively, it may also be a property that inhibits the growth of a specific pathogen. Examples of such properties include antitumor activity, prescribed differentiation-inducing activity, differentiation inhibitory activity, de-differentiation-inducing activity, cell growth (division) promoting activity, cell growth (division) inhibitory activity, anti-vascularization action, vascularization promoting action, immunosuppressive action, immune-enhancing action, anti-allergic action, anti-inflammatory action, hematopoiesis promoting action, psychotropic action, antidepressant action, hormonal action, anti-hormonal action, action promoting a specific enzymatic reaction, action inhibiting a specific enzymatic reaction, action promoting a specific signal transduction and action inhibiting a specific signal transduction. Alternatively, other examples include antibacterial action, antiviral action, antifungal action and anti-parasitic action. Additional examples include diabetes ameliorative action, hypertension ameliorative action, hyperlipidemia ameliorative action, antithrombotic action, analgesic action and diuretic action.

Thus, the exogenous substance can be an antitumor substance (anticancer substance), differentiation-inducing substance, differentiation-inhibiting substance, de-differentiation-inducing substance, cell growth (division) promoting substance, cell growth (division) inhibitory substance, anti-vascularization substance, vascularization promoting substance, immunosuppressive substance, immune-enhancing substance, anti-allergic substance, anti-inflammatory substance, hematopoiesis promoting substance, hormone, growth factor, enzyme, cytokine, chemokine, lipid mediator, psychotropic substance, vitamin, mineral, antibiotic, antiviral substance, antifungal substance or anti-parasitic substance. In addition, the exogenous substance can also be a composition containing these substances.

The exogenous substance can be, for example, a chemically synthesized substance. Since artificially synthesized compounds allow a desired compound to be comparatively readily available, they are preferable as application targets of the present invention. Examples of these artificially synthesized compounds include compounds obtained by developing substances derived from natural resources as lead substances, compounds obtained by artificially synthesizing substances equivalent to substances derived from natural resources, and artificially synthesized compounds designed to be unrelated to a substance derived from a natural resource. There are no particular limitations on the synthesis method, and the exogenous substance can be a substance obtained by ordinary chemical synthesis (and typically, organic synthesis) or biosynthesis (and typically, produced based on genetic engineering). Alternatively, the exogenous substance may be a natural extract. For example, the exogenous substance can be a substance extracted (and typically, isolated) from a human or an organism other than a human.

Preferable examples of the exogenous substance include amino acids, peptides, proteins, polynucleotides, virus particles, plasmids, gene transfer vectors, lipids and saccharides.

Here, there are no particular limitations on the peptides or proteins provided they are amino acid polymers having a plurality of polypeptide bonds. There are also no particular limitations on the number of amino acid residues contained in the peptide chain. In general, peptides have a comparatively low molecular weight, and the total number of amino acid residues is generally 100 or less (and preferably 60 or less such as 50 or less). Examples of these peptides and proteins include various types of antibodies, enzymes, hormones, cytokines, chemokines and cell surface factors.

There are no particular limitations on the polynucleotides provided they are polymers (nucleic acids) in which a plurality of nucleotides are linked by phosphodiester bonds. There are no particular limitations on the number of nucleotides that compose the polynucleotides and they may have a single strand or double strands. In addition, they may have a linear, cyclic or suitably folded shape. Examples thereof include RNA fragments (including mRNA, tRNA and microRNA) and DNA fragments of various lengths.

The amino acids, peptides, proteins, polynucleotides, virus particles, plasmids, gene transfer vectors, lipids and saccharides can be substances that have been artificially synthesized by chemical synthesis or biosynthesis (namely, produced based on genetic engineering). Alternatively, they may be substances that have been isolated from a human or organism other than a human.

A peptide (including protein) or RNA (such as mRNA or microRNA) derived from a cell can be contained in an exosome secreted from that cell and stably maintained therein (and typically, without being decomposed). Consequently, a peptide, protein or polynucleotide can be stably retained within the exosome for introducing an exogenous substance. In particular, these substances are susceptible to decomposition by proteases and nucleases present in the body (and typically, in the blood) as well as elimination by immune cells. In contrast, the stability of these peptides, proteins and polynucleotides in the body can be improved by enclosing them in the exosome for introducing an exogenous substance. The present invention can also be preferably applied to virus particles, plasmids and gene transfer vectors for the same reason.

In addition, the exosome for introducing an exogenous substance disclosed herein can preferably contain a highly hydrophobic substance for the exogenous substance contained in the exosome.

There are cases in which it is difficult to supply a desired amount of this highly hydrophobic substance to a cell culture broth due to the low solubility thereof. The amount of a hydrophobic substance supplied to cultured cells can be increased by containing the substance in the exosome for introducing an exogenous substance.

In addition, for reasons such as the highly hydrophobic substance being difficult to reach a desired concentration in the body (and typically, in the blood) or the highly hydrophobic substance being easily eliminated outside the body by metabolism or excretion, it tends to be necessary to administer the highly hydrophobic substance into the body (and typically, into the blood) at a high concentration or high frequency of administration. Stability in the body can be improved by enclosing the substance in the exosome for introducing an exogenous substance.

Alternatively, from the viewpoint of the health care industry, medical drugs containing substances such as doxorubicin having antitumor activity (and typically, anticancer drugs) or substances such as tacrolimus hydrate having immunosuppressive activity (and typically, immunosuppressants) as well as magnetic beads, quantum dots and other metallic diagnostic drugs are preferable as exogenous substances contained in the exosome for introducing an exogenous substance.

There are no particular limitations on the method used to enclose the substance inducing macropinocytosis and exogenous substance in the exosome, and an example thereof is electroporation. More specifically, a suspension is prepared in which an exosome, macropinocytosis-inducing substance and/or exogenous substance are suspended therein, and the suspension is loaded with a prescribed electric pulse to form fine holes in the exosome membrane, thereby enabling the macropinocytosis-inducing substance and/or exogenous substance to be introduced into the exosome.

The macropinocytosis-inducing substance and exogenous substance may be simultaneously contained (introduced) in the exosome or may be contained (introduced) separately by introducing over a plurality of times. From the viewpoints of procedural ease and avoiding coalescence of exosomes, the substance that induces macropinocytosis and the exogenous substance are preferably introduced simultaneously into the exosome.

The ratio at which the exosome, macropinocytosis-inducing substance and exogenous substance are suspended in the suspension can be suitably set corresponding to the type of substances introduced (contained) in the exosome and the amounts and composition of substances desired to be contained per exosome. The ratio between the exosome and macropinocytosis-inducing substance in the suspension is such that the ratio of exosome (g) to the substance inducing macropinocytosis (g) can be 1:0.1 to 1:5 (preferably 1:0.3 to 1:3 and more preferably 1:0.5 to 1:2, such as about 1:1). In addition, the ratio between the exosome and exogenous substance in the suspension (the total weight of all exogenous substances in the case of using two or more types of exogenous substances) is such that the ratio of exosome (g) to exogenous substance (g) is 1:0.1 to 1:10 (preferably 1:0.5 to 1:8 and more preferably 1:1 to 1:5, such as about 1:2). Here, the content (g) of exosome in the suspension is the content as the total amount of protein in the exosome.

Typically, a higher concentration of macropinocytosis-inducing substance can be contained in the exosome as the ratio of the content of the macropinocytosis-inducing substance in the suspension becomes higher relative to the exosome content in the suspension. Similarly, a higher concentration of the exogenous substance can be contained in the exosome as the ratio of the content of the exogenous substance in the suspension becomes higher relative to the exosome content in the suspension. In addition, the ratio of the macropinocytosis-inducing substance and exogenous substance contained in the exosome is typically proportional to the ratio of macropinocytosis-inducing substance and exogenous substance suspended in the suspension.

A composition used to introduce an exogenous substance into a target cell from outside the cell disclosed herein (composition for introducing an exogenous substance) contains an exosome containing one type or two or more types of an exogenous substance and a substance that induces macropinocytosis. Namely, the composition for introducing an exogenous substance contains the exosome for introducing an exogenous substance.

The composition for introducing an exogenous substance disclosed herein can contain various pharmacologically (pharmaceutically) acceptable carriers corresponding to the form of use provided the exosome and macropinocytosis-inducing substance can be retained in a state in which the exogenous substance contained in the exosome can be introduced into a target cell. Namely, the composition for introducing an exogenous substance disclosed herein is a composition in which an exogenous substance and macropinocytosis-inducing substance are retained in the exosomes in a state in which the activity thereof is not lost. A carrier commonly used in pharmaceuticals as a diluent or excipient and the like is preferable for the carrier. Although able to be suitably varied corresponding to the application or form of the composition for introducing an exogenous substance, typical examples of the carrier include water, physiological buffer and various organic solvents. The carrier can also be an aqueous solution having a suitable concentration of alcohol (such as ethanol), glycerol or non-drying oil such as olive oil. Alternatively, the carrier may be a liposome. In addition, examples of secondary components able to be contained in the composition for introducing an exogenous substance include various fillers, extenders, binding agents, moisturizers, surfactants, pigments and fragrances.

Alternatively, the composition for introducing an exogenous substance disclosed herein can be a composition containing an exosome containing one type or two or more types of an exogenous substance and a substance that induces macropinocytosis in a target cell. The composition for introducing an exogenous substance can contain various pharmacologically (pharmaceutically) acceptable carriers corresponding to the form of use provided the exosome contained in the exosome and macropinocytosis-inducing substance can be retained in a state in which the activity thereof is not lost. The previously described carriers can be used for the carrier without any particular limitations.

There are no particular limitations on the form of the composition for introducing an exogenous substance. Typical examples thereof include a liquid, suspension, emulsion, aerosol, foam, granules, powder, tablet, capsule, ointment and aqueous gel. In addition, the composition can also be in the form of a freeze-dried solid or granulated substance for preparing a drug solution by dissolving in physiological saline or suitable buffer (such as phosphate-buffered saline (PBS)) immediately before use.

Furthermore, the process per se for preparing various forms of medicinal agents (compositions) by using as material thereof an exosome containing an exogenous substance and a substance that induces macropinocytosis or an exosome (main component) containing an exogenous substance and a substance that induces macropinocytosis and various types of carrier (auxiliary component) is in compliance with conventionally known methods, and a detailed explanation of the preparation method per se is omitted since it does not characterize the present invention. Examples of sources of detailed information relating to formulation include Comprehensive Medicinal Chemistry, Corwin Hansch, ed., Pergamon Press (1990). The entire content of this publication is incorporated in the present description by reference.

There are no particular limitations on applicable target cells of the exosome for introducing an exogenous substance and composition for introducing an exogenous substance disclosed herein, and an exogenous substance can be introduced into various cells. Examples thereof include cells of humans and non-human animals (typically vertebrates and particularly mammals). The applicable target cells of the exosome for introducing an exogenous substance and composition for introducing an exogenous substance are particularly preferably human cells (human-derived cells).

For example, the cells can be cells present in various tissues of the body (derived from various tissues of the body), such as epidermal tissue, connective tissue, muscle tissue or nerve tissue. Furthermore, the applicable target cells are not limited to normal cells, but rather may also be causative cells of a disease such as tumor cells or pathogen-infected cells. In addition, there are also no particular limitations on the differentiated state of the target cells, and an exogenous substance can be preferably introduced into cells in various stages of differentiation, such as mature somatic cells, precursor cells, somatic stem cells or pluripotent stem cells.

Furthermore, the applicable target cells of the exosome for introducing an exogenous substance and composition for introducing an exogenous substance are not limited to cultured cells maintained outside the body, but rather cells present within the body are also applicable.

The applicable target cells of the exosome for introducing an exogenous substance and composition for introducing an exogenous substance disclosed herein are preferable cells in which macropinocytosis is induced by a macropinocytosis-inducing substance contained in the exosome for introducing an exogenous substance and composition for introducing an exogenous substance used (and typically, contained in an exosome). Typically, in the case of using a substance that induces macropinocytosis by stimulating a specific receptor for the macropinocytosis-inducing substance, the applicable target cells are preferably cells that express (and typically, highly express) a receptor that is stimulated by the macropinocytosis-inducing substance. For example, in the case of using a substance that stimulates EGFR for the macropinocytosis-inducing substance, cells expressing EGFR (and more preferably, cells highly expressing EGFR) are preferable for the target cells. In addition, in the case of using a substance that stimulates CXCR4 for the macropinocytosis-inducing substance, for example, cells expressing CXCR4 (and more preferably, cells highly expressing CXCR4) are preferable for the target cells. Similarly, in the case of using a substance that stimulates PDGFR for the macropinocytosis-inducing substance, cells expressing PDGFR (and more preferably, cells highly expressing PDGFR) are preferable for the target cells, and in the case of using a substance that stimulates FGFR and/or Syndecan-4 for the macropinocytosis-inducing substance, cells expressing at least one of FGFR and Syndecan-4 (and more preferably, cells highly expressing both FGFR and Syndecan-4) are preferable for the target cells. As a result, an exogenous substance can be efficiently introduced into the target cells.

In the case of applying the exosome for introducing an exogenous substance and composition for introducing an exogenous substance disclosed herein to cultured cells, there are no particular limitations on the applied cultured cells. For example, the cultured cells can be various types of cultured cells such as primary cultured cells, sub-cultured cells or cell lines of a human or non-human animal (and typically, a mammal).

The exosome for introducing an exogenous substance and composition for introducing an exogenous substance disclosed herein can be used in a method or dosage corresponding to the form and objective thereof.

For example, in the case of introducing an exogenous substance into cells cultured (sub-cultured) outside the body (in vitro), a suitable amount of the exosome for introducing an exogenous substance or composition for introducing an exogenous substance disclosed herein may be added to a medium containing target cells at any stage during the culturing process (such as an early stage after the start of culturing or after having cultured (grown) or sub-cultured for a prescribed period of time). There are no particular limitations on the added amount or number of additions since they can vary according to conditions such as type of cultured cells, cell density (cell density at the start of culturing), number of passages, culturing conditions or type of medium. Typically, the exosome for introducing an exogenous substance and composition for introducing an exogenous substance are preferably added one to several times (such as by adding at the start of culturing and additionally adding when sub-culturing the cells or when replacing the medium) so that exosome density in the medium is within the range of about 0.1 μg/mL to 100 μg/mL and preferably within the range of 0.2 μg/mL to 50 μg/mL (such as 0.4 μg/mL to 40 μg/mL).

In addition, the exosome for introducing an exogenous substance and composition for introducing an exogenous substance disclosed herein can also be used in combination with a substance having physiological activity other than the exogenous substance contained in the exosome (typically a substance having pharmacological activity).

Alternatively, the exosome for introducing an exogenous substance and composition for introducing an exogenous substance disclosed herein can also be supplied to a patient (namely, the body) in a desired amount thereof. There are no particular limitations on the administration method. Examples thereof include intravenous injection, intraarterial injection, intracutaneous injection, subcutaneous injection or intraperitoneal injection, oral administration, inhalation administration, transdermal administration, transmucosal administration and suppository administration. Alternatively, the exosome for introducing an exogenous substance and composition for introducing an exogenous substance disclosed herein may also be administered by a method in which it is embedded subdermally or subfascially in the form of an embedded preparation.

Furthermore, the target organism of administration of the exosome for introducing an exogenous substance and composition for introducing an exogenous substance can be a human or non-human animal (and typically, a mammal). The use of the exosome for introducing an exogenous substance or composition for introducing an exogenous substance targeted at a human is particularly preferable due to the high value thereof in the health care industry. In addition, the use of a laboratory animal such as a mouse, rat, guinea pig, rabbit, dog or cynomolgus monkey as an application target is preferable from the viewpoint of promoting various research and development. In addition, the use of a pet such as a dog or cat as an application target is preferable due to the high utility value thereof in the veterinary medicine industry.

In the case of administering the exosome for introducing an exogenous substance and composition for introducing an exogenous substance into the body, it is strongly required to ensure safety and reduce the immune response to the exosome and composition.

From the viewpoint of safety with respect to the exosome for introducing an exogenous substance (such as cytotoxicity attributable to the exosome for introducing an exogenous substance), the biological species of cells introduced with the exogenous substance using the exosome (the cells are also subsequently referred to as "recipient cells") and the biological species of the organism or cells from which the exosome is recovered (the organism is subsequently also referred to as the "donor organism" and the cells are also subsequently referred to as the "donor cells") are preferably the same. For example, in the case of introducing an exogenous substance into cells derived from a human, an exosome derived from a human (or human-derived cells) is used preferably. In addition, the recipient cells and donor cells (donor organism) are preferably the same biological species from the viewpoint of efficiently introducing the exosome for introducing an exogenous substance into target cells (recipient cells).

In addition, from the viewpoint of reducing an immune response to the exosome for introducing an exogenous substance, the human leukocyte antigen (HLA) type of the recipient cells is preferably the same as the HLA type of the donor cells (donor organism). Alternatively, the donor cells (donor organism) is preferably a homodonor for one of the two HLA possessed by the recipient cells. As a result, an immune response (immune rejection reaction) to the exosome for introducing an exogenous substance in the body introduced with the exosome for introducing an exogenous substance can be reduced (avoided). From the viewpoint of reducing the immune response to a higher degree, the recipient cells and the donor cells (donor organism) are preferably derived from the same body (individual). In other words, an exosome is preferably recovered from a body (and typically, a patient) introduced with an exogenous substance using the exosome for introducing an exogenous substance, and that exosome is preferably used for the exosome for introducing an exogenous substance (composition for introducing an exogenous substance).

According to the technology disclosed herein, by administering an exosome for introducing an exogenous substance (composition for introducing an exogenous substance) containing a substance having antitumor activity (and typically, an anticancer drug) for the exogenous substance to the body of a cancer patient, the substance having antitumor activity can be preferably introduced into the tumor cells. Namely, the use of a substance having antitumor activity for the exogenous substance enables the exosome for introducing an exogenous substance (composition for introducing an exogenous substance) according to the present invention to be used for the purpose of treating a tumor (cancer).

In addition, the exosome for introducing an exogenous substance (composition for introducing an exogenous substance) disclosed herein can be preferably used in a drug delivery system for introducing a substance having antitumor activity into tumor cells. In addition, according to the technology disclosed herein, the present invention is able to provide a method for treating a tumor comprising administration into the body of the exosome for introducing an exogenous substance (composition for introducing an exogenous substance) containing a substance having antitumor activity for the exogenous substance.

There are many cases in which tumor cells are in a state in which macropinocytosis is easily induced in order to take up nutrients present outside the cells into the cells. Typically, tumor cells frequently highly express EGFR, CXCR, PDGFR and/or FGFR. Consequently, as a result of using a substance that stimulates receptors thereof (typically, EGF, SDF-1, PDGF or FGF) as a macropinocytosis-inducing substance, macropinocytosis can be induced at a high level in tumor cells (and typically, tumor cells highly expressing EGFR, CXCR, PDGFR and/or FGFR). As a result, antitumor effects attributable to the exogenous substance contained in the exosome (and in this case, a substance having antitumor activity) can be selectively demonstrated against tumor cells (and typically, tumor cells highly expressing EGFR, CXCR, PDGFR and/or FGFR).

In addition, exosome particles having a diameter of about 50 nm to 100 nm have the property of easily accumulating in tumor tissue due to an enhanced permeability and retention effect (EPR effect). Consequently, antitumor effects attributable to an exogenous substance contained in an exosome (in this case, a substance having antitumor activity) can be selectively demonstrated against tumor cells. Here, the EPR effect refers to the property of substances of a specific size easily accumulating around tumor cells as a result of (I) particles having a particle diameter of several tens of nanometers to about 200 nm (and particularly, about 100 nm) easily infiltrating (penetrating) the periphery of tumor tissue due to the presence of gaps of about several hundred nanometers in the vascular walls (vascular endothelium) of newly formed blood vessels in tumor tissue (and typically, proliferating tumor tissue) and the periphery thereof, and (II) substances that have infiltrated (penetrated) the periphery of tumor tissue accumulating easily without being eliminated since lymph tissue is frequently immature.

For these reasons, supplying (and typically, administering into the body) the exosome for introducing an exogenous substance (composition for introducing an exogenous substance) containing a substance having antitumor activity according to the present invention to a tumor patient enables antitumor effects to be demonstrated at a high level while reducing adverse side effects on normal cells.

Furthermore, in the case of applying the exosome for introducing an exogenous substance according to the present invention to tumor cells, the present invention can be particularly preferably applied to an exogenous substance having a particle diameter of less than 20 nm (such as 5 nm or less, typically 1 nm or less and particularly 0.5 nm or less). Substances of this particle diameter inherently have difficulty in demonstrating the previously described EPR effect (or in other words, having difficulty in specifically accumulating (or being introduced) in tumor tissue) since they have a small particle diameter in comparison with substances that easily infiltrate (penetrate) the periphery of tumor cells by utilizing this EPR effect. However, containing a substance having a comparatively small particle diameter in this manner in an exosome makes it possible for the substance to achieve a particle diameter that facilitates specific accumulation in tumor tissue due to the EPR effect. As a result, antitumor effects of this exogenous substance can be specifically demonstrated in tumor cells.

Alternatively, by applying the exosome for introducing an exogenous substance containing a substance having differentiation-inducing activity (typically a differentiation inducer) for the exogenous substance (or composition for introducing an exogenous substance containing that exosome) to a stem cell (such as a pluripotent stem cell, somatic stem cell or precursor cell), that exosome (or composition for introducing an exogenous substance containing that exosome) can be used in regenerative medicine applications. Typically, by introducing a differentiation-inducing substance into a stem cell cultured (sub-cultured) outside the body (in vitro) using the exosome for introducing an exogenous substance (composition for introducing an exogenous substance) according to the present invention, that stem cell can be caused to differentiate in a desired cell. As a result, a desired cell, and typically a differentiated cell (including a cell aggregate, tissue or organ) and biosynthesis product derived from that cell, can be prepared (produced). This differentiated cell and the like can be preferably used as a material for regenerative medicine (and typically, as a cell material for transplant). For example, repair and regeneration can be effectively carried out by returning that differentiated cell and the like to patient requiring repair or regeneration (namely, returning to the body of the patient). In other words, various diseases for which tissue regeneration is an important method of treatment can be treated efficiently. Here, examples of biosynthesis products derived from differentiated cells produced by inducing differentiation from a stem cell as previously described include secretory proteins, hormones and other physiologically active substances (such as insulin).

Although the following provides an explanation of several examples relating to the present invention, the present invention is not intended to be limited to that indicated in these examples.

<Test 1: Preparation of Cell Culture (Sub-Culturing of Evaluation Target Cells)>

An evaluation test was carried out using the HeLa cells (derived from human cervical cancer), A431 cells (derived from human epidermoid carcinoma), MIA PaCa-2 cells (derived from human pancreatic cancer) and BxPC-3 cells (derived from human pancreatic cancer) shown in Table 1. All four types of these cells are human-derived cultured cell lines. These evaluation target cells were used after sub-culturing in the manner described below.

More specifically, each of the cells was disseminated in a culture dish having a diameter of 100 mm (100 mm dish) containing 10 mL of sub-culturing medium and cultured by allowing to stand undisturbed in an incubator under conditions of 5% $CO_2$ and 37° C. Media having the compositions shown in Table 1 were used for the sub-culturing media. The "medium" column in Table 1 indicates the type of medium used for sub-culturing each of the cells, the "additive" column in Table 1 indicates substances added to the media indicated in the "medium" column of Table 1 corresponding to each of the cells, and the "content" column in Table 1 indicates the content of "additive" contained in the sub-culturing media. Furthermore, (G) in Table 1 indicates that the manufacturer is "Life Technologies Corporation (Gibco)", (H) indicates that the manufacturer is "Thermo Fisher Scientific Inc. (Hyclone)", (S) indicates that the manufacturer is "Sigma-Aldrich Co. LLC.", and (W) indicates that the manufacturer is "Wako Pure Chemical Industries, Ltd.". In the following description, this media was used to culture each of the cells unless specifically indicated otherwise.

In addition, the target cells were sub-cultured once every two to three days in all cases. The cells were detached from the culture dishes by adding a mixture of trypsin (0.1 g/L) and ethylenediaminetetraacetic acid (EDTA, 0.11 mmol/L) (Nacalai Tesque, Inc.) to each culture dish at 2 mL/well followed by reacting for 5 minutes at 37° C.

TABLE 1

| Cells | | Composition of Sub-Culturing Medium | | |
|---|---|---|---|---|
| Cell Line | Origin | Medium | Additive | Content |
| HeLa | Human cervical cancer | α-MEM (G) | FBS (G) | 10% |
| A431 | Human epidermoid carcinoma | MEM (G) | FBS (G) | 10% |
| MIA PaCa-2 | Human pancreatic cancer | EMEM (W) | FBS (H) | 10% |
| | | | MEM non-essential amino acids (G) | 0.1 mM |
| | | | Penicillin (S) | 50 units/mL |
| | | | Streptomycin (S) | 50 μg/mL |
| BxPC-3 | Human pancreatic cancer | RPMI1640 (G) | FBS (H) | 10% |
| | | | Penicillin (S) | 50 units/mL |
| | | | Streptomycin (S) | 50 μg/mL |

<Test 2: Preparation of Exosome-Producing Cells>

A cell line stably expressing fused protein was established that was obtained by fusing an exosome marker protein in the form of CD63 with green fluorescent protein (GFP) (to also be simply referred to as "CD63-GFP"). Since exosomes recovered from this cell line exhibit green fluorescence due to the GFP fused to the CD63 protein, the presence of exosomes can be confirmed by observing this green fluorescence exhibited by GFP. Here, CD63-GFP-expressing gene was introduced into the cells by lipofection, and the cell line stably expressing CD63-GFP as described above was established by selecting those cells introduced with that gene using a suitable reagent. More specifically, this procedure was carried out in the manner described below.

First, CD63-GFP-expressing gene was prepared by purchasing pCT-CD63-GFP from System Biosciences, Inc. This pCT-CD63-GPF is constituted by a cytomegalovirus (CMV) promoter, gene encoding CD63-GFP and puromycin resistance gene loaded (inserted) into a lentivirus vector. In addition, Lipofectamine LTX Reagent was prepared for use as the lipofection reagent used in lipofection by purchasing from Life Technologies Corporation (Invitrogen).

Next, HeLa cells were disseminated in a 24-well culture dish (24-well dish) to a cell density of $4.7 \times 10^4$ cells/well followed by culturing for 1 day in an incubator under conditions of 5% $CO_2$ and 37° C. Medium having the same composition as the sub-culturing medium used to sub-culture the HeLa cells in Test 1 (to also be referred to as "HeLa medium") was used at 1.0 mL/well.

After culturing for 1 day as described above, the HeLa cells were cultured for 1 day in an incubator under conditions of 5% $CO_2$ and 37° C. after replacing the medium in each culture dish with 200 μL of HeLa medium containing a complex of pCT-CD63-GFP and Lipofectamine LTX Reagent to transfect the cells with CD63-GFP-expressing gene. The complex was prepared by mixing pCT-CD63-GFP and Lipofectamine LTX Reagent in accordance with the manual provided so that the content of pCT-CD63-GFP in the mixed solution was 800 ng/well and the content of Lipofectamine LTX Reagent was 1% by volume (1% (v/v)).

Next, the transfected cells were sub-cultured in 1 mL of HeLa medium containing 3 μg/mL of puromycin (Nacalai Tesque, Inc.) (to also be referred to as "p-HeLa medium"). As a result, cells were established that stably expressed CD63-GFP (to also be referred to as "CD63-GFP-HeLa").

<Test 3: Recovery of Exosomes>

Exosomes secreted into the medium by the CD63-GFP-HeLa cells prepared according to the method described above were recovered using these cells. Here, exosomes in the medium were separated and recovered by ultracentrifugation (Thery, C., Curr. Protoc. Cell Biol. (2006), Chapter 3, Unit 3.22) or Total Exosome Isolation (from cell culture media) (Life Technologies Corporation (Invitrogen)). More specifically, this procedure was carried out in the manner described below.

First, the CD63-GFP-HeLa cells were disseminated in a culture dish having a diameter of 10 cm (100 mm dish) at a cell density of $2 \times 10^6$ cells/well followed by culturing for 1 day in an incubator under conditions of 5% $CO_2$ and 37° C. The p-HeLa medium was used for the medium at 10 mL/well.

After culturing for 1 day as described above, the medium in the culture dish containing the CD63-GFP-HeLa cells was removed and the inside of the culture dish was washed five times using α-MEM medium (5 mL). As a result, exosomes able to be contained in the medium (typically, FBS) were able to be removed from the culture dish. Subsequently, α-MEM medium (Life Technologies Corporation (Gibco)) containing 10% exosome-free FBS (exosome-depleted FBS Media Supplement, System Biosciences, Inc.) and 3 μg/mL of puromycin was added at 10 mL/well followed by culturing for 3 to 4 days under conditions of 5% $CO_2$ and 37° C. Medium in the culture dish was recovered after culturing for this predetermined amount of time.

Next, exosomes secreted into the medium recovered in the manner described above were separated and recovered by ultracentrifugation. More specifically, a series of procedures including centrifuging for 10 minutes at 300×g and 4° C., centrifuging the supernatant for 10 minutes at 2,000×g and 4° C., followed by additionally centrifuging the supernatant for 30 minutes at 10,000×g and 4° C. was carried out to precipitate non-viable cells able to be suspended in the medium. After carrying out this centrifugation procedure, the supernatant was recovered, and a centrifugation procedure including centrifuging the supernatant for 70 minutes under conditions of 100,000×g and 4° C. was repeated twice to precipitate the exosomes. Subsequently, exosomes secreted into the medium by the CD63-GFP-HeLa cells (to also be referred to as "CD63-GFP exosomes") were recovered by recovering the precipitate. The resulting exosomes were dispersed in Dulbecco's Phosphate-Buffered Saline (DPBS, Nacalai Tesque, Inc.) for use as an exosome stock solution.

Alternatively, exosomes were separated and recovered in the recovered medium after culturing for the prescribed amount of time described above using Total Exosome Isolation (from cell culture media) (Life Technologies Corporation (Invitrogen)). This Total Exosome Isolation (from cell culture media) refers to a commercially available kit for isolating exosomes from a cell culture broth, and the specific procedure was carried out as described in the manual provided with the kit.

The density of the recovered exosome was quantified using a BCA Protein Assay Kit (Thermo Fisher Scientific Inc. (Pierce)). Protein density obtained using this quantification procedure (μg/mL) was treated as exosome density (μg/mL). Furthermore, the presence and form of the exosomes were confirmed by detecting an exosome marker protein (such as CD63 or CD9) by western blotting or observation using a transmission electron microscope (negative staining).

<Test 4: Introduction (Inclusion) of Exogenous Substance into Exosome>

An exogenous substance and substance that induces macropinocytosis were introduced into the exosomes obtained in Test 3 (CD63-GFP exosomes). Saporin (Sigma-Aldrich Co. LLC., to apply similarly hereinafter) was used for the exogenous substance and EGF (Sigma-Aldrich Co. LLC., to apply similarly hereinafter) was used for the substance that induces macropinocytosis. In addition, transferrin (Sigma-Aldrich Co. LLC., to be apply similarly hereinafter), which is known to induce clathrin-dependent endocytosis, was contained in the endosomes as a comparative example. Electroporation was used for the method for introducing these substances into the exosomes. The details of this test are as described below.

A dispersion was prepared in which 25 μg of CD63-GFP exosomes and 50 μg of saporin and/or 25 μg of EGF were dispersed in 100 μL of DPBS. Alternatively, a dispersion was prepared in which 25 μg of CD63-GFP exosomes and 25 μg of transferrin were dispersed in 100 μL of DPBS. Electroporation was then carried out on these dispersions using the Super Electroporator NEPA21 Type II manufactured by NEPA Gene Co., Ltd. Electroporation was carried out under conditions including the use of two pulses of 200 V and 5 msec for the poring pulse, five pulses at 20 V and 50 msec for the transfer pulse and a 1 cm electroporation cuvette at 25° C.

Following this electroporation, the resulting solution was filtered with an Amicon Ultra Centrifugal Filter (100 kDa) manufactured by Merck Millipore Corporation to remove any saporin, EGF and transferrin not introduced (contained) in the exosomes. This filtration was carried out by a centrifugation procedure for 10 minutes under conditions of 18,000×g and 4° C., and exosomes that remained on the filter were recovered. Exosomes obtained following this filtration procedure were subjected to a washing procedure including dispersing the exosomes in 500 μL of DPBS followed by centrifuging for 10 minutes under conditions of 18,000×g and 4° C. that was repeated twice. Exosomes containing saporin and/or EGF or exosomes containing transferrin were prepared as described above. The resulting exosomes were dispersed in DPBS for use as an exosome stock solution.

In the following description, the CD63-GFP exosomes obtained in Test 3 are designated as Sample 1, the saporin-containing exosomes obtained in Test 4 are designated as Sample 2, the EGF-containing exosomes obtained in Test 4 are designated as Sample 3, the EGF and saporin-containing exosomes obtained in Test 4 are designated as Sample 4, and the transferrin-containing exosomes obtained in Test 4 are designated as Sample 5. The exosomes of Samples 1 to 5 are summarized in Table 2.

TABLE 2

| Sample | Exosomes | Exogenous Substance |
|---|---|---|
| 1 | CD63-GFP exosomes | None |
| 2 | CD63-GFP exosomes | Saporin |
| 3 | CD63-GFP exosomes | EGF |
| 4 | CD63-GFP exosomes | EGF, saporin |
| 5 | CD63-GFP exosomes | Transferrin |

<Test 5: Exosome Uptake Test>

Uptake of the exosomes of Sample 1 by the test cells when these exosomes and a substance that induces macropinocytosis in the form of EGF were supplied to medium containing the test cells was evaluated by observing fluorescence using a confocal microscope. A431 cells were used for the test cells. Details of this test are as described below.

First, A431 cells were disseminated in a glass culture dish having a diameter of 35 mm at a cell density of $2.0 \times 10^5$ cells/well followed by pre-culturing for 1 day in an incubator under conditions of 5% $CO_2$ and 37° C. Medium having the same composition as that used for the sub-culturing medium for A431 cells in Test 1 was used for the medium (to also be referred to as "A431 medium") at 2 mL/well.

After culturing (pre-culturing) for 1 day as described above, a procedure including removing the medium containing the A431 cells from the culture dish and washing the inside of the culture dish using 1 mL of FBS-free A431 medium (namely, MEM medium) was repeated three times. Subsequently, 20 μg/mL of the exosomes according to Sample 1 and MEM medium containing 500 nM EGF were added at 200 μL/well followed by culturing for 24 hours under conditions of 5% $CO_2$ and 37° C. In addition, a group in which 20 μg/mL of the exosomes according to Sample 1 were added was provided for use as a control group, while a group in which EGF was not added was also provided (EGF non-addition group).

Hoechst 33342 (Life Technologies Corporation (Invitrogen)) was added to the cells cultured in the presence of exosomes at 5 μg/mL as the amount present in the culture broth followed by allowing to stand for 15 minutes under conditions of a temperature of 37° C. to stain the nuclei of the cells. After staining the nuclei in this manner, the cells were washed three times using the A431 medium (1 mL). 1 mL of A431 medium was then added to the culture dish followed by observing fluorescence using a confocal microscope without fixing the target cells (namely, while in the state of viable cells). The FV1200 manufactured by Olympus Corporation was used to observe fluorescence.

The results of observing fluorescence with the confocal microscope (confocal laser scanning microscope) for each test group are shown in FIG. 1. These images depict micrographs (images) captured for investigating the uptake of exosomes of Sample 1 into cells in each test group. More specifically, the micrographs (images) shown on the left (CD63-GFP exosome column) are micrographs captured for investigating the localization of the exosomes according to Sample 1. In addition, the micrographs (images) shown in the right column (Merge column) are merged images obtained by superimposing (merging) nuclear staining images obtained using Hoechst 33342 with the images captured for investigating the localization of the exosomes according to Sample 1 shown in the left column.

As shown in FIG. 1, the test group cultured following addition of EGF (EGF addition group, lower row of FIG. 1) demonstrated more intense GFP fluorescence in comparison with the EGF non-addition group (upper row of FIG. 1). This indicates that the EGF addition group takes up exosomes more actively in comparison with the EGF non-addition group. On the basis of these results, the supply of EGF to target cells was confirmed to be able to promote uptake of exosomes into the cells by the cells.

<Test 6: Exosome Uptake Test>

Uptake of the exosomes of Sample 1 by the test cells when these exosomes and a substance that induces macropinocytosis in the form of EGF were supplied to medium containing the test cells was evaluated by analyzing using a flow cytometer. A431 cells were used for the test cells. Details of this test are as described below.

First, A431 cells were disseminated in a 24-well culture dish (24-well plate) at a cell density of $4.7 \times 10^4$ cells/well followed by pre-culturing for 1 day in an incubator under conditions of 5% $CO_2$ and 37° C. A431 medium was used for the test medium at 1.0 mL/well.

After culturing (pre-culturing) for 1 day as described above, the medium in the culture dish was removed and the inside of the culture dish was washed three times using MEM medium (200 μL). Subsequently, media having the composition shown in Table 3 were added at 200 μL/well followed by culturing for 24 hours under conditions of 5% $CO_2$ and 37° C. More specifically, MEM medium (namely, A431 medium not containing FBS) containing EGF and exosomes according to Sample 1 at the concentrations shown in Table 3 was used in test groups 6-1 to 6-3. In addition, A431 medium (namely, MEM medium containing 10% FBS) containing EGF and the exosomes according to Sample 1 at the concentrations shown in Table 3 was used in test groups 6-4 and 6-5.

TABLE 3

| Test Group | FBS Concentration (%) | Exosome (Sample 1) Concentration (μg/mL) | EGF Concentration (nM) |
|---|---|---|---|
| 6-1 | 0 | 20 | 0 |
| 6-2 | 0 | 20 | 100 |
| 6-3 | 0 | 20 | 500 |
| 6-4 | 10 | 20 | 0 |
| 6-5 | 10 | 20 | 500 |

The cells were washed three times using DPBS (200 µL) following culturing in the presence of exosomes. Subsequently, a mixture of trypsin (0.1 g/L) and ethylenediaminetetraacetic acid (EDTA, 0.11 mol/L) (Nacalai Tesque, Inc.) was added to the culture dish at 200 µl/well followed by reacting for 10 minutes at 37° C. to detach the cells. The detached cells were recovered in centrifuge tubes followed by centrifuging for 5 minutes at 800×g and 4° C. and removing the supernatant. Next, 400 µL aliquots of DPBS were added to each centrifuge tube and the cells were suspended in the DPBS followed by again centrifuging for 5 minutes under conditions of 800×g and 4° C. and removing the supernatant. The cells of each test group were then each suspended in 400 µL of DPBS.

The cell suspensions of each test group prepared in the manner described above were analyzed using a flow cytometer. Guava easyCyte manufactured by Merck Millipore Corporation was used for the flow cytometer. More specifically, the average GFP fluorescence intensity per cell in each test group was measured by detecting GFP fluorescence under conditions of an excitation wavelength of 488 nm and emission wavelength of 525 nm.

The results of the analysis using the flow cytometer as described above are shown in FIG. 2. The graph shown in FIG. 2 indicates relative values of average GFP fluorescence intensity per cell of each test group based on a value of 100 for the average GFP fluorescence intensity per cell in test group 6-1 (control group). The bars of the graph shown in FIG. 2 indicate the results of test groups 6-1, 6-2, 6-3, 6-4 and 6-5 in order from left to right.

Figure 2:
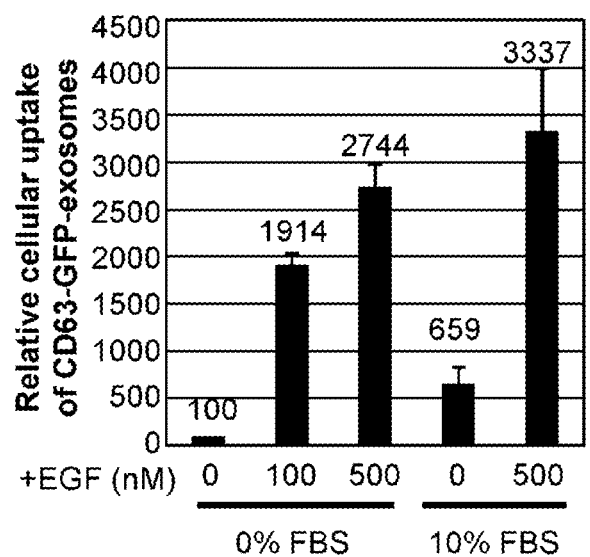
FIG. 2 is a graph indicating the results of an analysis using a flow cytometer to investigate the uptake of exosomes by target cells (A431 cells) when supplying exosomes (Sample 1) to the target cells in a test example and culturing the target cells while changing the medium conditions (presence or absence of FBS and concentration of EGF) by analyzing using a flow cytometer. The graph indicates average GFP fluorescence intensity per cell in each test group as a relative value of average GFP fluorescence intensity per cell in a control group (test group cultured under medium conditions including the absence of FBS and the absence of EGF). Average values obtained when the same test was independently repeated three times are represented by the bars of the graph and standard deviations (±SD) are indicated with the error bars.

As shown in FIG. 2, average GFP fluorescence intensity per cell in test groups 6-2 and 6-3 was remarkably higher in comparison with average GFP fluorescence intensity per cell in test group 6-1. In addition, this average GFP fluorescence intensity per cell increased as the concentration of EGF in the medium increased (namely, increased dependent on the concentration of EGF in the medium). More specifically, the average GFP fluorescence intensity per cell in test group 6-2 was about 19 times greater than the average GFP fluorescence intensity per cell in test group 6-1, while the average GFP fluorescence intensity per cell in test group 6-3 was about 27 times greater. On the basis of these results, supplying EGF to the target cells was confirmed to remarkably promote uptake of exosomes into the cells.

In addition, as shown in FIG. 2, the average GFP fluorescence intensity per cell in test group 6-5 was remarkably higher in comparison with the average GFP fluorescence intensity per cell in test groups 6-1 and 6-4. More specifically, the average GFP fluorescence intensity per cell in test group 6-5 was about 33 times greater than the average GFP fluorescence intensity per cell in test group 6-1 and about five times higher than that in test group 6-4. Namely, on the basis of the results for test groups 6-1 to 6-5, supplying EGF to the target cells was confirmed to be able to promote uptake of exosomes into the cells irrespective of the presence or absence of FBS in the medium.

Since test groups 6-4 and 6-5 contain exosomes derived from FBS in the medium, the exosomes derived from FBS are in competition with the exosomes according to Sample 1. This competitive state was reproduced in an in vitro experimental system in which endogenous exosomes (exosomes intrinsically present in the body) compete with the exosomes for introducing an exogenous substance (composition for introducing an exogenous substance) according to the present invention when the exosomes for introducing an exogenous substance were supplied (administered) into the body. Namely, according to the results of test groups 6-4 and 6-5, uptake of the target exosome (namely, exosome for introducing an exogenous substance) was able to be promoted considerably by supplying EGF to the target cells even in an environment in which endogenous exosomes (in this case, exosomes derived from FBS) are present.

<Test 7: Evaluation Test of Macropinocytosis-Inducing Activity of EGF>

Whether or not uptake of exosomes into cells promoted by the supply of EGF to target cells is attributable to macropinocytosis was evaluated by observing fluorescence using a confocal microscope. More specifically, the intracellular localization of a marker substance that identifies uptake of a substance by macropinocytosis and the intracellular localization of the exosomes according to Sample 1 were compared by observing fluorescence using a confocal microscope. In this test, dextran (approximately 70 kDA polysaccharide), which is known to be taken up into cells by macropinocytosis, was used for the marker substance that identifies uptake of a substance by macropinocytosis. A431 cells were used for the test cells. Details of this test are as indicated below.

More specifically, analysis was carried out according to the same conditions and procedure as Test 5 with the exception of using medium containing EGF (500 nM), exosomes according to Sample 1 (20 µg/mL) and dextran at a concentration of 0.5 mg/mL during culturing in the presence of exosomes. Here, dextran (Texas red-dextran, Life Technologies Corporation (Molecular Probe)) labeled with a fluorescent dye (Texas red) was used for the dextran.

Figure 3:
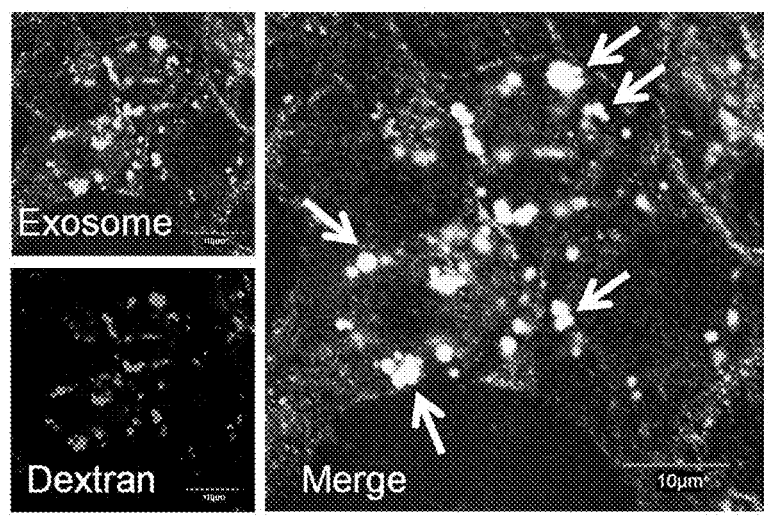
FIG. 3 depicts micrographs (images) obtained using a confocal laser scanning microscope for investigating the uptake of exosomes and dextran by target cells (A431 cells) when exosomes (Sample 1) and dextran were supplied to the target cells in a test example and then cultured in the presence of EGF. The micrograph (image) shown in the upper left (Exosome) is a fluorescent light micrograph for investigating the localization of exosomes by fluorescent observation. In addition, the micrograph (image) shown in the lower left (Dextran) is a fluorescent light micrograph for investigating the localization of dextran by fluorescent observation. The micrograph (image) shown on the right (Merge) is an image obtained by superimposing (merging) the image shown in the upper left (Exosome) with the image shown in the lower left (Dextran). The arrows in the micrographs (images) indicate typical examples of regions where exosomes and dextran are both located within the cells. Furthermore, the scales shown in the micrographs are all 10 μm.

The results of observing fluorescence with a confocal microscope (confocal laser scanning microscope) are shown in FIG. 3. These images are micrographs (images) captured for investigating uptake of the exosomes according to Sample 1 and the Texas red-dextran into the test cells. More specifically, the micrograph (image) shown on the upper left is a micrograph captured for investigating the localization of the exosomes according to Sample 1. The micrograph (image) shown on the lower left is an image indicating the localization of Texas red-dextran. In addition, the micrograph (image) shown on the right is an image obtained by superimposing (merging) the image for investigating the localization of the exosomes according to Sample 1 shown on the upper left with the image for investigating the localization of Texas red-dextran shown on the lower left.

As shown in FIG. 3, intracellular localization of the exosomes according to Sample 1 coincided with the intracellular localization of the dextran. Namely, the exosomes according to Sample 1 and the dextran were co-localized in the cells. This indicates that the mechanism by which exosomes and dextran are taken up into cells is the same, or in other words, that exosomes and dextran are taken up into cells by macropinocytosis. On the basis of these results, the uptake of exosomes into cells promoted by supplying EGF to target cells was confirmed to be attributable to macropinocytosis. In other words, macropinocytosis was confirmed to be induced by EGF and uptake of exosomes into the cells was confirmed to be promoted as a result thereof. Namely, EGF was confirmed to be able to be preferably used as a substance that induces macropinocytosis.

<Test 8: Evaluation Test of Macropinocytosis-Inducing Activity of EGF>

Whether or not uptake of exosomes into cells promoted by the supply of EGF to target cells is attributable to macropinocytosis was evaluated by analysis using a flow cytometer. More specifically, the effect of an inhibitor of macropinocytosis on uptake of exosomes was analyzed using a flow cytometer. In this test, 5-(N-ethyl-N-isopropyl)

amiloride (EIPA, Sigma-Aldrich Co. LLC.) was used for the macropinocytosis inhibitor. A431 cells were used for the test cells. Details of this test are as indicated below.

First, A431 cells were prepared by pre-culturing for 1 day using the same conditions and procedure as Test 6 followed by washing the cells three times using MEM medium. MEM medium containing 100 nM EIPA were added at 200 µL per well followed by allowing to stand for 30 minutes under conditions of 5% $CO_2$ and 37° C. Next, EGF in an amount resulting in a concentration thereof in the medium of 100 nM and the exosomes according to Sample 1 in an amount resulting in a concentration thereof in the medium of 20 µg/mL were added to the EIPA-containing MEM medium followed by culturing for 3 hours under conditions of 5% $CO_2$ and 37° C. This test group was designated as the EIPA treatment group. Furthermore, a test group treated in the same manner as the EIPA treatment group with the exception of not adding the EIPA to the MEM medium was provided as a control (EIPA non-treatment group).

Cells following culturing in the presence of the exosomes were analyzed using a flow cytometer according to the same conditions and procedure as Test 6.

Figure 4:
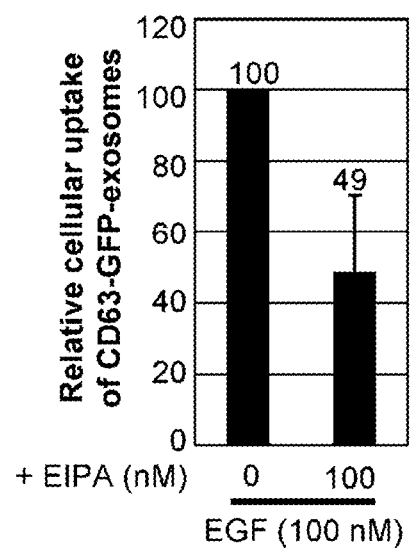
FIG. 4 is a graph indicating the results of an analysis using a flow cytometer to investigate the uptake of exosomes by target cells (A431 cells) when the cells were cultured in medium containing a macropinocytosis inhibitor in the form of 5-(N-ethyl-N-isopropyl) amiloride (also referred to as "EIPA") and subsequently cultured by supplying exosomes (Sample 1) to the target cells in a test example. The graph indicates average GFP fluorescence intensity per cell in an EIPA treatment group as a relative value of average GFP fluorescence intensity per cell in a control group (non-EIPA treatment group). Average values obtained when the same test was independently repeated three times are represented by the bars of the graph and standard deviations (±SD) are indicated with the error bars.

The results are shown in FIG. 4. The graph shown in FIG. 4 indicates the relative values of average GFP fluorescence intensity per cell of the EIPA treatment group based on a value of 100 for the average GFP fluorescence intensity per cell in the EIPA non-treatment group.

As shown in FIG. 4, average GFP fluorescence intensity per cell of the EIPA treatment group was considerably lower (about 50% or less) in comparison with the average GFP fluorescence intensity per cell of the EIPA non-treatment group. This indicates that the uptake of exosomes by target cells was inhibited by culturing after adding a macropinocytosis inhibitor in the form of EIPA. Namely, this indicates that the macropinocytosis-inducing activity of EGF was inhibited by EIPA. On the basis of these results, the uptake of exosomes into cells promoted by the supply of EGF to target cells was confirmed to be attributable to macropinocytosis. In other words, macropinocytosis of the cells was confirmed to be induced by the supply of EGF to target cells, and uptake of exosomes into the cells was confirmed to be promoted as a result thereof. Namely, EGF was confirmed to be able to be preferably used as a substance that induces macropinocytosis.

<Test 9: Evaluation Test of Cell Viability>

Cell viability when target cells were cultured after supplying with the exosomes according to Sample 1 was evaluated by carrying out a cell growth test (WST-1 assay) by absorption photometry using 4-[3-(4-iodophenyl)-2-(4-nitrophenyl)-2H-5-tetrazolio]-1,3-benzene disulfonate (WST-1, water-soluble tetrazolium salt). A431 cells were used for the test cells. Details of the evaluation test are as indicated below.

A431 cells were disseminated in each well of a 96-well plate so that the number of cells was about $1.2 \times 10^4$ cells/well followed by culturing (pre-culturing) for 1 day in an incubator under conditions of 5% $CO_2$ and 37° C. A431 medium was used for the medium and the amount of medium per well was 100 µL.

After culturing (pre-culturing) for the prescribed amount of time indicated above, the medium in each well of the culture dish was replaced with MEM medium (namely, A431 medium not containing FBS) containing 20 µg/mL of the exosomes according to Sample 1 and 0 nM (namely, absence of addition of EGF), 100 nM or 500 nM EGF. The amount of medium per well was 50 µL. Furthermore, a test group not containing either the exosomes according to Sample 1 or EGF in the medium was provided as a control group.

After supplying exosomes to the cells as described above, the 96-well plate was placed in a $CO_2$ incubator followed by final culturing under conditions of 37° C. and 5% $CO_2$. Viability of the test cells (number of viable cells) was measured using a commercially available colorimetric kit (Premix WST-1 Cell Proliferation Assay System, Takara Bio Inc.) at the point 24 hours after the start of culturing (final culturing) in the presence of exosomes. Namely, the number of cells was measured by measuring the amount of water-soluble formazan in the medium by absorption photometry (measurement wavelength: 450 nm, control wavelength: 620 nm) by utilizing the formation of water-soluble formazan following reduction of tetrazolium salt in the reagent by the enzymatic activity of viable cells. Furthermore, the procedure other than that described in detail below was carried out in accordance with the manual provided with the assay kit.

More specifically, reagent containing a chromogenic substrate in the form of "water-soluble tetrazolium salt (WST-1)" was added to the cell culture wells after the prescribed amount of culturing time had elapsed at 10 µL/well followed by incubating for 45 minutes under conditions of 5% $CO_2$ and 37° C. Subsequently, absorbance at a wavelength of 450 nm ($A_{450}$) and absorbance at a wavelength of 620 nm ($A_{620}$) were measured for the cell culture broths to which the chromogenic reagent had been added using a spectrophotometer (microplate reader) followed by calculation of the value for $A_{450-620}$ by correcting $A_{450}$ with $A_{620}$ to calculate cell viability of each test group. The relative value of cell viability (%) of each test group was then calculated according to the following equation based on a value of 100% for the cell viability of the control group: cell viability (%)= ($A_{450-620}$ of each test group)÷($A_{450-620}$ of control group)× 100. The results are shown in FIG. 5.

Figure 5:
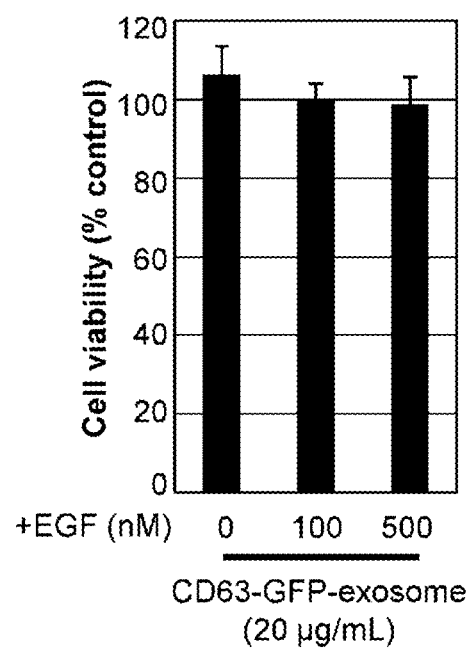
FIG. 5 is a graph indicating the results of investigating the cell viability (%) of target cells (A431 cells) when exosomes (Sample 1) were supplied to the target cells in a test example and then cultured while changing the concentration of EGF in the medium. The graph indicates cell viability (%) in each test group as a relative value of cell viability (%) in a control group (test group cultured under conditions including not adding exosomes or EGF). Average values obtained when the same test was independently repeated three times are represented by the bars of the graph and standard deviations (±SD) are indicated with the error bars.

As shown in FIG. 5, cell viability was nearly unchanged in comparison with the control group in each of the test groups cultured following the further addition of EGF at 0 nM, 100 nM or 500 nM in addition to the exosomes according to Sample 1 (there are no significant differences in cell viability). On the basis thereof, the exosomes according to Sample 1 (namely, CD63-GFP exosomes) and EGF added to the medium (supplied to the target cells) were confirmed to not have any effect on the growth of the target cells. Namely, the CD63-GFP exosomes taken up into the medium and cells were confirmed to be free of cytotoxicity and cell growth promoting activity. In addition, cell growth of the target cells was confirmed to not be accelerated by EGF added to the medium in addition to the CD63-GFP exosomes.

<Test 10: Test of Introduction of Exogenous Substance into Cells Using Exosomes>

The efficiency at which an exogenous substance contained in exosomes is supplied to the cells was evaluated using the exosomes according to Sample 2. More specifically, the efficiency at which saporin contained in exosomes is taken up into cells was evaluated by using saporin for the exogenous substance and investigating cell viability when exosomes containing saporin were supplied to the cells. Saporin is a type of protein toxin (namely, a type of substance having antitumor activity), and cells that have taken up saporin are known to undergo cell death. Namely, lower cell viability indicates more efficient introduction of saporin into cells.

The test method included measuring cell viability (%) of test cells according to the same conditions and procedure as Test 9 with the exception of changing culturing in the presence of exosomes (final culturing) to the conditions indicated below. Namely, in this test, conditions were the same as those of Test 9 with the exception of replacing the medium in the culture dish following pre-culturing with A431 medium (namely, MEM medium containing 10% FBS) containing 4 μg/mL of the exosomes according to Sample 2 (namely, saporin-containing exosomes) or 7 μg/mL of saporin and EGF at 0 nM (namely, EGF non-addition) or 500 nM, and culturing same for 48 hours. Here, each test group was designated test groups 10-1 to 10-4. Furthermore, a test group not containing any of the exosomes (exosomes according to Sample 2, or in other words, saporin-containing exosomes), saporin or EGF in the medium was provided as a control group. The compositions of the media used for final culturing of each test group are summarized in Table 4.

TABLE 4

| Test Group | Exosome (Sample 2) Concentration (μg/mL) | Saporin Concentration (μg/mL) | EGF Concentration (nM) |
|---|---|---|---|
| 10-1 | 4 | 0 | 0 |
| 10-2 | 4 | 0 | 500 |
| 10-3 | 0 | 7 | 0 |
| 10-4 | 0 | 7 | 500 |
| Control | 0 | 0 | 0 |

Figure 6:
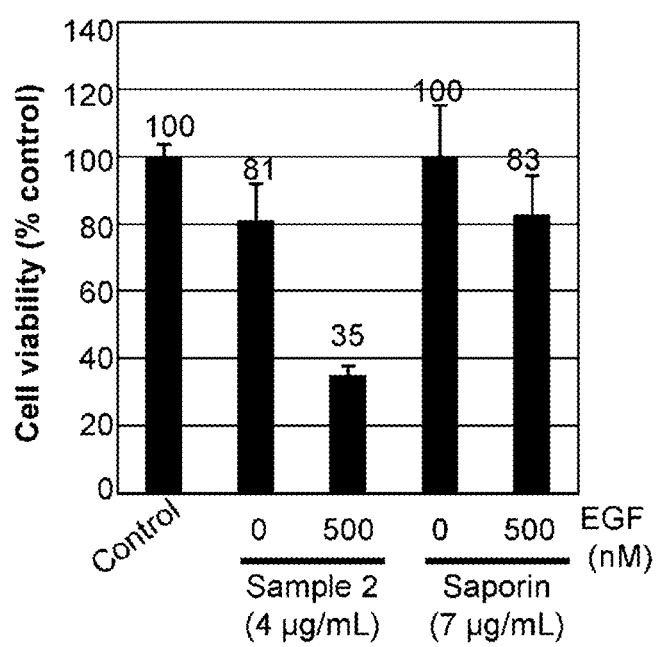
FIG. 6 is a graph indicating the results of investigating the cell viability (%) of target cells (A431 cells) when exosomes (Sample 2) or saporin was supplied to the target cells in a test example and then cultured in the presence or absence of EGF. The graph indicates cell viability (%) in each test group as a relative value of cell viability (%) in a control group (test group cultured under conditions including not adding exosomes, saporin or EGF). Average values obtained when the same test was independently repeated three times are represented by the bars of the graph and standard deviations (±SD) are indicated with the error bars.

Relative values of cell viability (%) of each test group following the final culturing were calculated based on a value of 100% for the cell viability of the control group using the same procedure as Test 9. The results are shown in FIG. 6. Here, the bars of the graph indicate the results for the control group and test groups 10-1, 10-2, 10-3 and 10-4 in order from left to right.

As shown in FIG. 6, test group 10-2 demonstrated remarkably low cell viability in comparison with the other test groups (control group, test group 10-1, test group 10-3 and test group 10-4) (cell viability was about less than half of that of the other test groups). This indicates that saporin was introduced into the cells of test group 10-2 with particularly high efficiency in comparison with the other test groups. Moreover, based on a comparison of results between test group 10-1 and test group 10-2 and a comparison of results between test group 10-3 and test group 10-4, uptake of saporin into the cells was confirmed to be able to be promoted more by suppling EGF to the target cells in comparison with not adding EGF. This indicates that EGF is able to highly efficiently induce macropinocytosis in the test cells.

Here, according to the results of test group 10-3, hardly any saporin was confirmed to be taken up (introduced) into the cells in the case of only adding saporin to the medium. In contrast, based on a comparison of results between test group 10-1 and test group 10-3 and a comparison of results between test group 10-2 and test group 10-4, the saporin was confirmed to be able to be highly efficiently introduced into the target cells by allowing exosomes to contain saporin.

On the basis of these results, an exogenous substance was confirmed to be able to be highly efficiently introduced into target cells by supplying the target cells with exosomes containing the exogenous substance and a substance that induces macropinocytosis.

<Test 11: Cell Uptake Test of Exosomes Containing EGF>

Uptake of the exosomes by target cells was evaluated by analyzing using a flow cytometer using the exosomes according to Sample 3 (namely, EGF-containing exosomes). A431 cells were used for the test cells. Details of this test are as described below.

First, A431 cells pre-cultured for 1 day were prepared according to the same conditions and procedure as Test 6 followed by washing the cells three times using MEM medium. A431 medium (MEM medium containing 10% FBS) containing 20 μg/mL of CD63-GFP exosomes (namely, Sample 1), 20 μg/mL of EGF-containing exosomes (namely, Sample 3) or 20 μg/mL of transferrin (Tf)-containing exosomes (namely, Sample 5) was added at 200 μL per well followed by culturing for 24 hours under conditions of 5% $CO_2$ and 37° C. Each of the test groups was referred to as the Sample 1 addition group, Sample 3 addition group and Sample 5 addition group, respectively.

Following culturing in the presence of exosomes as described above, the cells were analyzed using a flow cytometer according to the same conditions and procedure as Test 6.

Figure 7:
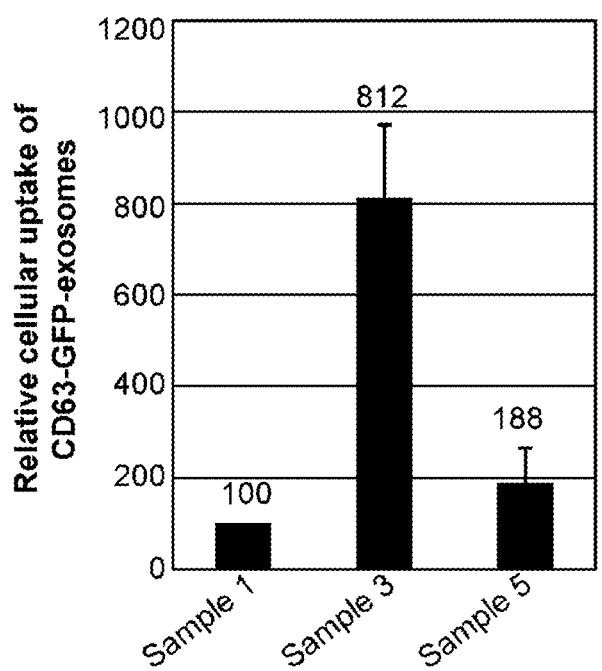
FIG. 7 is a graph indicating the results of an analysis using a flow cytometer to investigate the uptake of exosomes by target cells (A431 cells) when the cells were cultured by supplying exosomes (Samples 1, 3 and 5) to the cells in a test example. The graph indicates average GFP fluorescence intensity per cell in each test group as a relative value of average GFP fluorescence intensity per cell in a Sample 1 addition group. Average values obtained when the same test was independently repeated three times are represented by the bars of the graph and standard deviations (±SD) are indicated with the error bars.

The results are shown in FIG. 7. The bars of the graph shown in FIG. 7 indicate relative values of average GFP fluorescence intensity per cell of the Sample 3 addition group and Sample 5 addition group based on a value of 100 for the average GFP fluorescence intensity per cell of the Sample 1 addition group.

As shown in FIG. 7, average GFP fluorescence intensity per cell in the Sample 3 addition group was considerably higher in comparison with the average GFP fluorescence intensity per cell in the Sample 1 addition group. More specifically, the average GFP fluorescence intensity per cell in the Sample 3 addition group was about eight times higher than the average GFP fluorescence intensity per cell in the Sample 1 addition group. This indicates that macropinocytosis was inducted in the target cells by the exosomes (and typically, EGF contained in the exosomes) as a result of supplying exosomes containing EGF to the target cells, and that uptake of exosomes by the cells was promoted as a result thereof. Namely, by supplying the target cells with exosomes containing a substance that induces macropinocytosis in the target cells, macropinocytosis was confirmed to be able to be preferably induced in the target cells and uptake of the exosomes into the target cells was confirmed to be able to be promoted by the induction of macropinocytosis.

In addition, although average GFP fluorescence intensity per cell in the Sample 5 addition group increased slightly (by about 1.9 times) in comparison with the average GFP fluorescence intensity per cell in the Sample 1 addition group, the increase was not as remarkable as in the Sample 3 addition group. In other words, average GFP fluorescence intensity per cell in the Sample 3 addition group was higher than the average GFP fluorescence intensity per cell in the Sample 5 addition group (about 4.3 times higher). Here, transferrin refers to a substance that clathrin-dependently induces endocytosis by stimulating transferrin receptors. Namely, based on a comparison between the Sample 3 addition group and Sample 5 addition group, exosomes were confirmed to be taken up into cells more efficiently by macropinocytosis than by clathrin-dependent endocytosis.

<Test 12: Test of Introduction of Exogenous Substance into Cells Using EGF-Containing Exosomes>

The efficiency at which an exogenous substance contained in exosomes is introduced into cells was evaluated using the exosomes according to Sample 2 (namely, exosomes containing saporin) and exosomes according to Sample 4 (namely, exosomes containing both EGF and saporin). More specifically, the efficiency at which saporin contained in exosomes is taken up into cells was evaluated by using saporin for the exogenous substance and investigating cell viability when exosomes containing saporin were supplied to the cells. A431 cells were used for the test cells. Details of the test are as indicated below.

The test method included measuring cell viability (%) of test cells according to the same conditions and procedure as Test 10 with the exception of changing culturing in the presence of exosomes to the conditions indicated below. More specifically, cell viability of the test cells was measured according to the same conditions and procedure as Test 10 with the exception of replacing the medium in the culture dishes with A431 medium (namely, MEM medium containing 10% FBS) containing the exosomes according to Sample 2 or Sample 4 at 0.4 μg/mL, 4 μg/mL or 20 μg/mL, and culturing same for 72 hours. Furthermore, a test group not containing exosomes according to Sample 2 or Sample 4 in the medium was provided as a control group.

Relative values of cell viability (%) of each test group were calculated for each test group following culturing in the presence of exosomes as described above based on a value of 100% for cell viability in the control group. The results are shown in FIG. 8.

In addition, the morphology of the cells after culturing for 72 hours in the presence of exosomes was observed for the cells of each of the test groups using a light microscope (phase contrast microscope). The results of microscopically observing each test group are shown in FIG. 9.

Figure 8:
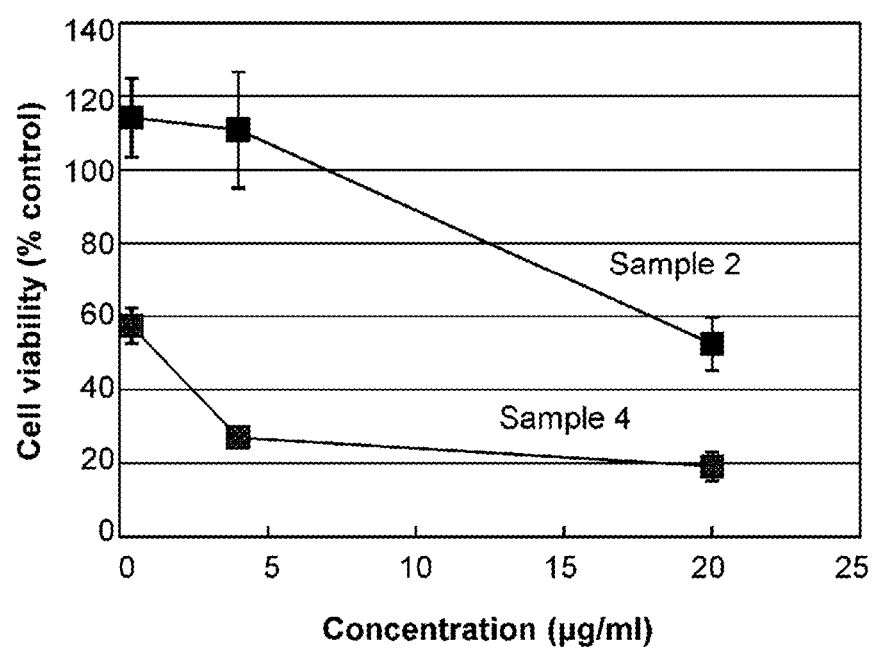
FIG. 8 is a graph indicating the results of investigating the cell viability (%) of target cells (A431 cells) when the target cells were cultured by supplying exosomes (Sample 2 or 4) to the target cells in a test example. The graph indicates the exosome density in the medium on the horizontal axis and cell viability (%) in each test group on the vertical axis as a relative value of cell viability (%) in a control group (test group cultured under conditions including not adding exosomes and not adding EGF). Average values obtained when the same test was independently repeated three times are represented by each plot and standard deviations (±SD) are indicated with the error bars.

As shown in FIG. 8, cells of the Sample 4 addition group demonstrated lower cell viability in comparison with cells of the control group and cells of the Sample 2 addition group of the same density. In addition, in the case exosome density in the medium for Sample 4 was at least within the range of 0.4 μg/mL to 20 μg/mL, cell viability of target cells supplied with the exosomes was confirmed to decrease, and this cell viability was confirmed to decrease (dependent on the concentration of exosomes according to Sample 4) as density in the medium of the exosomes according to Sample 4 increased. Cell viability decreased considerably particularly in the case exosome density in the medium was 4 μg/mL or more (4 μg/mL to 20 μg/mL).

Figure 9:
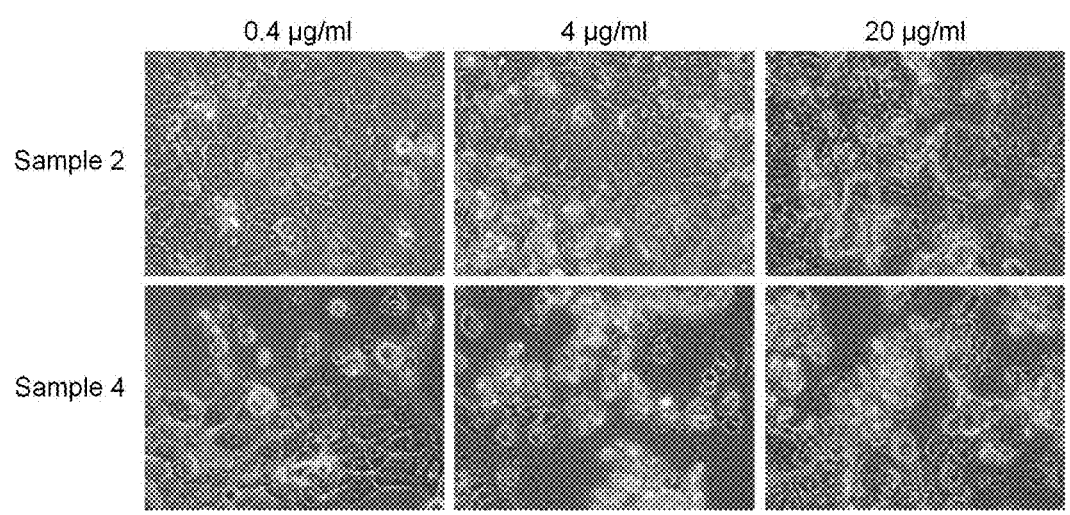
FIG. 9 depicts micrographs (images) observed using a light microscope of the morphology of target cells (A431 cells) when the target cells were cultured by supplying exosomes (Sample 2 or 4) to the target cells in a test example. The concentrations shown in the figure (μg/mL) indicate the exosome density in the medium.

In addition, as shown in FIG. 9, the morphology of the cells of the Sample 4 addition group lacked uniformity in comparison with the cells of the Sample 2 addition group of the same density (in that, typically, the size of the cells becomes smaller and the borders of the cells become indistinct), and many of the cells were observed to emit white color. Those cells having non-uniform cell morphology that are observed to emit white color are cells that have undergone cell death (or are undergoing cell death).

These findings indicate that the use of exosomes containing EGF makes it possible to efficiently introduce saporin contained in exosomes into target cells. On the basis of these results, the use of exosomes containing a substance that induces macropinocytosis and an exogenous substance was confirmed to enable the exogenous substance to be efficiently introduced into the target cells. In other words, exosomes containing a substance that induces macropinocytosis and an exogenous substance were confirmed to be able to be preferably used for the purpose of introducing the exogenous substance into target cells.

<Test 13: Exosome Uptake Test>

The uptake of exosomes by test cells was evaluated under the condition of the presence of exosomes and a substance that induces macropinocytosis by extending the duration of culturing under those conditions. The evaluation method included observing fluorescence using a confocal microscope and analyzing using a flow cytometer. A431 cells were used for the test cells. Details of the test are as indicated below.

The analysis using a flow cytometer was carried out in the manner indicated below. Pre-cultured cells were cultured for 96 hours in the presence of exosomes in the same manner as Test 6 with the exception of replacing the medium with A431 medium (namely, MEM medium containing 10% FBS) containing 20 μg/mL of the exosomes according to Sample 1 and EGF at 100 nM or 500 nM followed by culturing in the medium while adding an equal concentration of EGF (100 nM or 500 nM) every 24 hours (namely, 24 hours, 48 hours, 72 hours and 96 hours after the start of culturing in the presence of exosomes). In addition, a test group (to also be referred to as an "EGF non-addition group") not containing EGF in the medium (containing the exosomes according to Sample 1 at 20 μg/mL) was provided as a control group.

Figure 10:
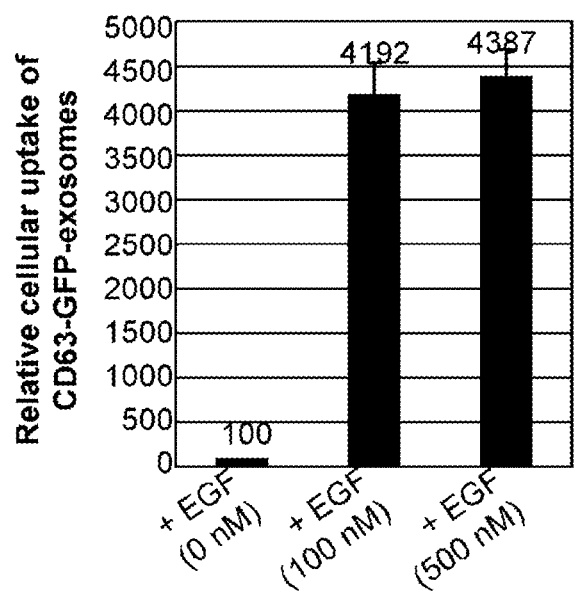
FIG. 10 is a graph indicating the results of an analysis using a flow cytometer to investigate the uptake of exosomes by target cells (A431 cells) when the exosomes (Sample 1) were supplied to the target cells in a test example and then cultured for 96 hours while changing the concentration of EGF in the medium. The graph indicates average GFP fluorescence intensity per cell in each test group as a relative value of average GFP fluorescence intensity per cell in a control group (EGF non-addition group). Average values obtained when the same test was independently repeated three times are represented by the bars of the graph and standard deviations (±SD) are indicated with the error bars.

Uptake of exosomes by cells was evaluated for the cells of each test group after the final culturing in the presence of exosomes by analyzing the cells using a flow cytometer according to the same procedure as Test 6. The results are shown in FIG. 10. The bars of the graph shown in FIG. 10 indicate relative values of the average GFP fluorescence intensity per cell of each test group based on a value of 100 for the average GFP fluorescence intensity per cell in the EGF non-addition group.

Figure 11:
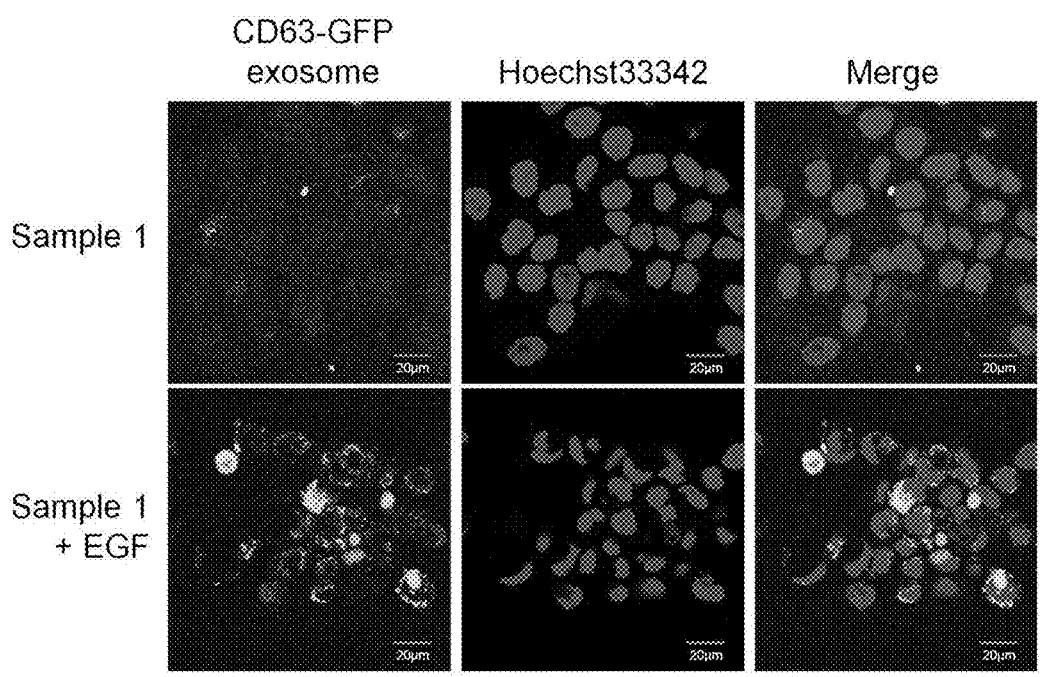
FIG. 11 depicts micrographs (images) captured using a confocal laser scanning microscope for investigating the uptake of exosomes by target cells (A431 cells) when exosomes (Sample 1) were supplied to the target cells in a test example and then cultured for 96 hours in the presence or absence of EGF. The micrographs (images) shown in the left column (CD63-GFP exosome column) are fluorescent light micrographs (FL images) for investigating the localization of exosome by fluorescent observation. The micrographs (images) shown in the middle column (Hoechst 33342 column) are nuclear staining images obtained using Hoechst 33342. In addition, the micrographs (images) shown in the right column (Merge column) are images obtained by superimposing (merging) the FL images shown in the left column with the nuclear staining images shown in the middle column. Furthermore, the scales shown in the micrographs are all 20 μm.

In addition, uptake of exosomes by test cells was evaluated for the cells of each of the test groups by observing fluorescence using a confocal microscope according to the same procedure as Test 5. The results of fluorescence observation for the test group in which EGF was added at 500 nM and the EGF non-addition group are shown in FIG. 11. These images are micrographs (images) for investigating the uptake of the exosomes according to Sample 1 into cells for each test group. The results for the test group in which EGF was added at 500 nM are shown in the lower row, while the results for the EGF non-addition group are shown in the upper row. More specifically, the micrographs (images) shown in the left column are micrographs captured for investigating localization of the exosomes according to Sample 1. The micrographs (images) shown in the middle column are images obtained by nuclear staining with Hoechst 33342. In addition, the micrographs (images) shown in the right column are images obtained by superimposing (merging) the images captured for investigating the localization of the exosomes according to Sample 1 shown in the left column with the images obtained by nuclear staining with Hoechst 33342 shown in the middle column.

As shown in FIGS. 10 and 11, target cells cultured for a long period of time in the presence of the exosomes according to Sample 1 and EGF were confirmed to demonstrate considerably high uptake of exosomes in comparison with cells of the EGF non-addition group (about 40 times more). In particular, when the results of Test 6 are compared with the results of flow cytometer analysis in this test, a larger number of exosomes were confirmed to be able to be taken up (introduced) into the target cells as a result of culturing for a long period of time in the presence of the exosomes according to Sample 1 and EGF. On the basis of these results, an exogenous substance was confirmed to be able to be efficiently introduced into target cells by adjusting the amount of time the exosome for introducing an exogenous substance disclosed herein (namely, the composition for introducing an exogenous substance) is supplied to the target cells (supply interval).

<Test 14: Exosome Uptake Test Using MIA PaCa-2 Cells for Test Cells>

Uptake of exosomes by test cells was evaluated in the case of using MIA PaCa-2 cells for the test cells. The evaluation method included observing fluorescence using a confocal microscope and analyzing using a flow cytometer. Furthermore, the exosomes according to Sample 1 were used for the exosomes. Details of the test are as indicated below.

Uptake of exosomes by test cells was evaluated by analyzing using a flow cytometer according to the same conditions and procedure as Test 6 with the exception of using MIA PaCa-2 cells for the test cells and changing conditions during culturing in the presence of exosomes. More specifically, uptake was evaluated according to the same procedure as Test 6 with the exception of culturing pre-cultured MIA PaCa-2 cells for 24 hours in medium containing 20 μg/mL of the exosomes according to Sample 1 and EGF at 0 nM (namely, absence of addition of EGF) or 500 nM, and using medium having the same composition as the medium used for sub-culturing MIA PaCa-2 cells for pre-culturing and culturing in the presence of exosomes (to also be referred to as "MIA PaCa-2 medium").

Figure 12:
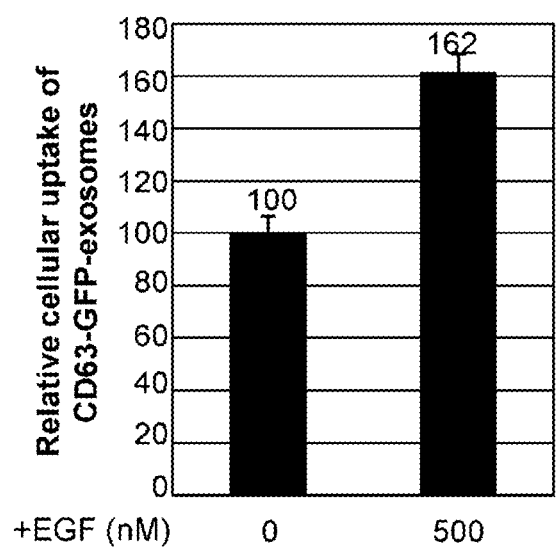
FIG. 12 is a graph indicating the results of an analysis using a flow cytometer to investigate the uptake of exosomes (Sample 1) by target cells according to a test example when MIA PaCa-2 cells were used for the target cells. The graph indicates average GFP fluorescence intensity per cell in each test group as a relative value of average GFP fluorescence intensity per cell in a control group (EGF non-addition group). Average values obtained when the same test was independently repeated three times are represented by the bars of the graph and standard deviations (±SD) are indicated with the error bars.

The results are shown in FIG. 12. Bars of the graph shown in FIG. 12 indicate the relative values of average GFP fluorescence intensity per cell of the EGF addition group based on a value of 100 for the average GFP fluorescence intensity per cell in the EGF non-addition group (control group).

Figure 13:
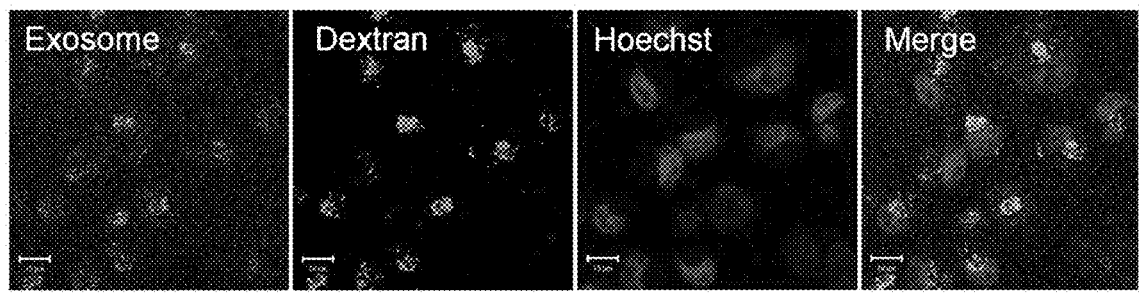
FIG. 13 depicts micrographs (images) captured using a confocal laser scanning microscope for investigating the uptake of exosomes (Sample 1) and dextran by target cells according to a test example when MIA PaCa-2 cells were used for the target cells. The micrograph (image) shown on the far left (Exosome) is a fluorescent light micrograph (image) for investigating the localization of exosomes by fluorescent observation. The micrograph (image) shown second from the left (Dextran) is a fluorescent light micrograph (image) for investigating the localization of dextran by fluorescent observation. The micrograph (image) shown second from the right (Hoechst 33342) is a nuclear staining image obtained using Hoechst 33342. In addition, the micrograph (image) shown in the right column (Merge column) is an image obtained by superimposing (merging) the image shown on the far left (Exosome), the image shown second from the left (Dextran), and the nuclear staining image shown second from the right. Furthermore, the scales shown in the micrographs are all 10 μm.

In addition, the uptake of exosomes by cells (MIA PaCa-2 cells) was evaluated for cells of the EGF addition group by observing fluorescence using a confocal microscope. Furthermore, cells cultured in MIA PaCa-2 medium, for 24 hours, containing 20 μg/mL of the exosomes according to Sample 1, 500 nM EGF and dextran labeled with a fluorescent dye (Texas red) having a concentration of 0.5 mg/mL (Texas red-dextran) were used for the cells used for observing fluorescence. Observation of fluorescence using a confocal microscope was carried out according to the same procedure as Test 5. The results are shown in FIG. 13. These images are micrographs (images) captured for investigating the uptake of the exosomes according to Sample 1 and dextran into the cells. More specifically, the micrograph (image) on the far left is a micrograph for investigating the localization of the exosomes according to Sample 1. The micrograph (image) shown second from the left is an image indicating the localization of Texas red-dextran. The micrograph (image) shown second from the right is an image obtained by nuclear staining with Hoechst 33342. In addition, the micrograph (image) on the far right is an image obtained by superimposing (merging) the image for investigating localization of exosomes shown on the far left, the image for investigating the localization of Texas red-dextran shown second from the left, and the image obtained by nuclear staining with Hoechst 33342 shown second from the right.

As shown in FIGS. 12 and 13, uptake of exosomes was confirmed to be promoted by EGF even in the case of using MIA PaCa-2 cells for the test cells (namely, target cells). This indicates that macropinocytosis is able to be induced by EGF even in the case of using MIA PaCa-2 cells for the target cells.

<Test 15: Exosome Uptake Test Using BxPC-3 Cells for Test Cells>

Uptake of exosomes by test cells was evaluated in the case of using BxPC-3 cells for the test cells. The evaluation method included analyzing the cells using a flow cytometer. Furthermore, the exosomes according to Sample 1 were used for the exosomes. Details of the test are as indicated below.

Uptake of exosomes by test cells was evaluated by analyzing using a flow cytometer according to the same conditions and procedure as Test 6 with the exception of using BxPC-3 cells for the test cells and changing conditions during culturing in the presence of exosomes. More specifically, uptake was evaluated according to the same procedure as Test 6 with the exception of culturing pre-cultured BxPC-3 cells for 24 hours in medium containing 20 μg/mL of the exosomes according to Sample 1 and EGF at 0 nM (namely, absence of addition of EGF) or 500 nM, and using medium having the same composition as the medium used for sub-culturing BxPC-3 cells for pre-culturing and culturing in the presence of exosomes (to also be referred to as "BxPC-3 medium").

Figure 14:
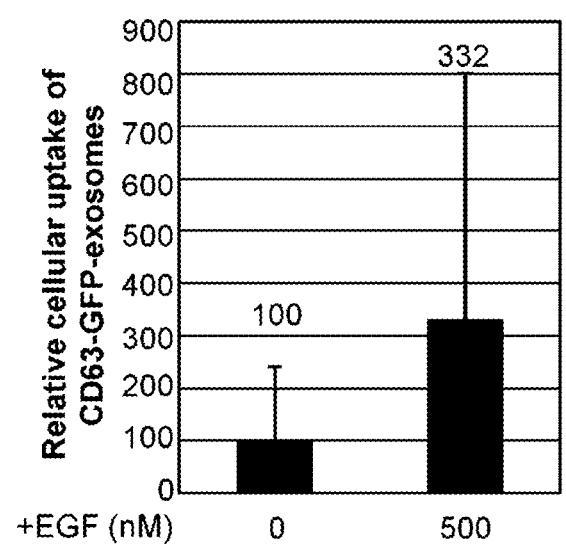
FIG. 14 is a graph indicating the results of an analysis using a flow cytometer to investigate the uptake of exosomes (Sample 1) by target cells according to a test example when BxPC-3 cells were used for the target cells. The graph indicates average GFP fluorescence intensity per cell in each test group as a relative value of average GFP fluorescence intensity per cell in a control group (EGF non-addition group). Average values obtained when the same test was independently repeated three times are represented by the bars of the graph and standard deviations (±SD) are indicated with the error bars.

The results are shown in FIG. 14. Bars of the graph shown in FIG. 14 indicate the relative values of average GFP fluorescence intensity per cell of the EGF addition group based on a value of 100 for the average GFP fluorescence intensity per cell in the EGF non-addition group (control group).

As shown in FIG. 14, uptake of exosomes was confirmed to be promoted by EGF even in the case of using BxPC-3 cells for the test cells (namely, target cells). This indicates that macropinocytosis is able to be induced by EGF even in the case of using BxPC-3 cells for the target cells.

Based on the results Tests 14 and 15, the results of tests using A431 cells for the test cells are not phenomena unique to the A431 cells, but rather were confirmed to be applicable to other cells as well (typically, human-derived cells, and generally tumor cells and particularly MIA PaCa-2 cells and BxPC-3 cells). Namely, the results of Tests 14 and 15 indicate that the target cells in the present invention are not limited to A431 cells, and that an exogenous substance contained in an exosome can be preferably introduced into other cells as well (typically, human-derived cells, and generally tumor cells and particularly MIA PaCa-2 cells and BxPC-3 cells) by inducing macropinocytosis in the test cells by supplying a substance that induces macropinocytosis thereto. In addition, even in the case of using cells other than A431 cells (typically, human-derived cells, and generally tumor cells and particularly MIA PaCa-2 cells and BxPC-3 cells) for the target cells of the present invention, an exogenous substance contained in an exosome was shown to be able to be efficiently introduced into target cells by supplying the target cells with a substance that induces macropinocytosis and exosomes containing that exogenous substance.

<Test 16: Macropinocytosis Induction Test of SDF>

Uptake of endosomes by test cells was evaluated by analysis using a flow cytometer in the case of using SDF for the substance that induces macropinocytosis. The exosomes according to Sample 1 were used for the exosomes. In addition, HeLa cells were used for the test cells. The details of the test are as indicated below.

First, HeLa cells were disseminated in a 24-well culture dish (24-well plate) at 4.7×10$^4$ cells/well followed by culturing for 1 day in an incubator under conditions of 5% $CO_2$ and 37° C. HeLa medium was used for the medium at 1.0 mL/well.

After culturing (pre-culturing) the HeLa cells for 1 day as described above, the medium in the culture dish was removed and the inside of the culture dish was washed three times using α-MEM medium (200 μL). Subsequently, medium containing 20 μg/mL of the exosomes according to Sample 1 and SDF at 100 nM or 200 nM was added at 200 µL per well followed by culturing (final culturing) for 24 hours under conditions of 5% $CO_2$ and 37° C. HeLa medium (namely, containing 10% FBS) was used for the medium. In addition, a test group (to also be referred to as the "SDF non-addition group") not containing SDF in the medium (containing 20 µg/mL of the exosomes according to Sample 1) was provided as a control group.

Figure 15:
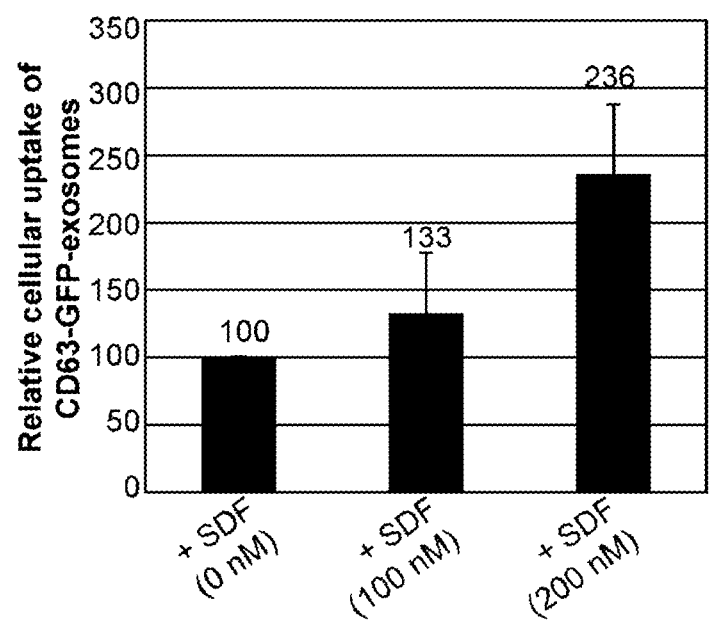
FIG. 15 is a graph indicating the results of an analysis using a flow cytometer to investigate the uptake of exosomes (Sample 1) by target cells (HeLa cells) when the exosomes were supplied to the target cells in a test example and then cultured while changing the SDF concentration in the medium. The graph indicates average GFP fluorescence intensity per cell in each test group as a relative value of average GFP fluorescence intensity per cell in a control group (SDF non-addition group). Average values obtained when the same test was independently repeated three times are represented by the bars of the graph and standard deviations (±SD) are indicated with the error bars.

After culturing in the presence of exosomes as described above, uptake of exosomes by target cells was analyzed using a flow cytometer for the HeLa cells in the same manner as Test 6. The results are shown in FIG. 15. The bars of the graph of FIG. 15 indicate relative values of average GFP fluorescence intensity per cell of each test group based on a value of 100 for the average GFP fluorescence intensity per cell in the SDF non-addition group.

As shown in FIG. 15, the average GFP fluorescence intensity per cell in the SDF addition groups was higher in comparison with average GFP fluorescence intensity per cell in the SDF non-addition group. In addition, average GFP fluorescence intensity per cell in the SDF addition groups was confirmed to increase as the concentration of SDF in the medium became higher (increased dependent on the concentration of SDF in the medium). This indicates that macropinocytosis can be induced by supplying target cells with SDF. Namely, SDF was indicated to be a substance that induces macropinocytosis in the same manner as EGF. Based on these results, SDF was confirmed to be able to be preferably used as a substance that induces macropinocytosis.

INDUSTRIAL APPLICABILITY

As has been described above, according to the art disclosed herein, an exogenous substance (and typically, a substance having pharmacological activity) can be efficiently introduced into target cells by utilizing the uptake of exosomes by macropinocytosis. In addition, the art disclosed herein provides a composition for efficiently introducing an exogenous substance (and typically, a substance having pharmacological activity) into target cells, and an exosome able to efficiently introduce an exogenous substance into target cells, by utilizing the uptake of exosomes by macropinocytosis.

Consequently, the art disclosed herein can be preferably used in a drug delivery system for introducing an exogenous substance (and typically, a substance having pharmacological activity) into a target cell. For example, the art disclosed herein can be preferably used in the fields of cancer therapy and regenerative medicine by using a substance having anticancer (antitumor) action or a substance having differentiation-inducing action as an exogenous substance.

The invention claimed is:

1. A method for introducing an exogenous substance into a target cell in vitro, the method comprising:
   preparing a cell culture containing the target cell,
   preparing a dispersion containing isolated exosomes,
   introducing both an exogenous substance and a macropinocytosis-inducing substance into the inside of the exosomes in the dispersion, wherein the exogenous substance and the macropinocytosis-inducing substance are added to the dispersion and introduced into the inside of the exosomes in the dispersion by electroporation, and wherein the macropinocytosis-inducing substance is epidermal growth factor (EGF);
   supplying the exosomes having the exogenous substance and the macropinocytosis-inducing substance introduced into the inside of the exosomes into the cell culture containing the target cell;
   after the supplying, culturing the cell culture containing the target cell in the presence of the exosomes, wherein the exosomes are taken up into the target cell from an outside of the target cell by macropinocytosis during the culturing; and
   after the culturing, investigating an uptake of the exosomes in the target cell.

2. The method according to claim 1, wherein the exogenous substance has pharmacological activity.

3. The method according to claim 1, wherein the target cell is a human tumor cell and the exogenous substance is a compound having antitumor activity.

4. The method according to claim 1, wherein
   the isolated exosomes comprise exosomes recovered from a broth of a cell culture containing exosome-producing cells; and
   the exosome-producing cells express a fused protein, in which an exosome marker protein is fused with a green fluorescent protein, and wherein
   the step of investigating comprises confirming presence of the exosomes in the target cell by observing green fluorescence exhibited by the green fluorescent protein.

5. The method according to claim 4, wherein the exosome marker protein is a protein selected from the group consisting of CD9; CD63 and CD81.

6. The method according to claim 4, wherein the observing step comprises observing the green fluorescence with a confocal microscope and/or a flowcytometer.

7. The method according to claim 1, wherein the macropinocytosis in the culturing is confirmed by using dextran and/or 5-(N-ethyl-N-isopropyl)amiloride.

* * * * *